(12) United States Patent
Anglese

(10) Patent No.: US 10,888,387 B2
(45) Date of Patent: Jan. 12, 2021

(54) ARTICULATION MECHANISMS FOR SURGICAL INSTRUMENTS SUCH AS FOR USE IN ROBOTIC SURGICAL SYSTEMS

(71) Applicant: COVIDIEN LP, Mansfield, MA (US)

(72) Inventor: Kurt J. Anglese, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 174 days.

(21) Appl. No.: 16/276,826

(22) Filed: Feb. 15, 2019

(65) Prior Publication Data
US 2020/0261167 A1  Aug. 20, 2020

(51) Int. Cl.
*A61B 34/30* (2016.01)
*A61B 34/00* (2016.01)
(Continued)

(52) U.S. Cl.
CPC .............. *A61B 34/30* (2016.02); *A61B 17/29* (2013.01); *A61B 34/71* (2016.02);
(Continued)

(58) Field of Classification Search
CPC .... A61B 18/1442; A61B 2017/320071; A61B 2017/2927; A61B 2017/2943;
(Continued)

(56) References Cited

U.S. PATENT DOCUMENTS 5,752,973 A   5/1998  Kieturakis
5,792,135 A   8/1998  Madhani et al.
(Continued)

FOREIGN PATENT DOCUMENTS

WO   2017136710 A2   8/2017

OTHER PUBLICATIONS

Wu et al., "Design of a Modular Continuum-Articulated Laparoscopic Robotic Tool with Decoupled Kinematics", IEEE Robotics and Automation Letters, vol. 4, No. 4, Oct. 2019, pp. 3545-3552.
(Continued)

*Primary Examiner* — Katherine M Shi
*Assistant Examiner* — Alyssa M Keane
(74) *Attorney, Agent, or Firm* — Carter, DeLuca & Farrell LLP

(57) ABSTRACT

An articulation assembly for a surgical instrument, surgical instrument including the same, and robotic surgical system including a surgical robot and the surgical instrument including the articulation assembly. The articulation assembly includes lead screw assemblies each including a lead screw and a collar operably engaged about the lead screw such that rotation of the lead screw translates the collar about the lead screw. Articulation cables are operably coupled to the collars of the lead screw assemblies such that proximal movement of one of the collars about the respective lead screw tensions the corresponding articulation cable and such that distal movement of one of the collars about the respective lead screw de-tensions the corresponding articulation cable. Proximal gear assemblies are coupled to the lead screws. Coupling gears couple pairs of the proximal gear assemblies with one another to maintain a pre-tension on the corresponding articulation cables.

20 Claims, 17 Drawing Sheets

(51) Int. Cl.
*A61B 17/29* (2006.01)
*A61B 90/50* (2016.01)
*A61B 18/14* (2006.01)
*A61B 17/00* (2006.01)

(52) U.S. Cl.
CPC .......... *A61B 18/1442* (2013.01); *A61B 90/50* (2016.02); *A61B 2017/00398* (2013.01); *A61B 2017/00473* (2013.01); *A61B 2017/00477* (2013.01); *A61B 2017/2927* (2013.01); *A61B 2034/305* (2016.02)

(58) Field of Classification Search
CPC .......... A61B 2034/301–306; A61B 2034/715; A61B 90/50; A61B 34/30; A61B 34/70; A61B 34/71; B25J 18/00; B25J 9/102
See application file for complete search history.

(56) References Cited

U.S. PATENT DOCUMENTS

| | | | |
|---|---|---|---|
| 5,848,986 | A | 12/1998 | Lundquist et al. |
| 6,817,974 | B2 | 11/2004 | Cooper et al. |
| 7,799,028 | B2 | 9/2010 | Schechter et al. |
| 7,861,906 | B2 | 1/2011 | Doll et al. |
| 7,918,230 | B2 | 4/2011 | Whitman et al. |
| 8,579,176 | B2 | 11/2013 | Smith et al. |
| 9,055,961 | B2 | 6/2015 | Manzo et al. |
| 9,474,569 | B2 | 10/2016 | Manzo et al. |
| 2002/0099371 | A1 | 7/2002 | Schulze et al. |
| 2002/0177842 | A1 | 11/2002 | Weiss |
| 2003/0125734 | A1 | 7/2003 | Mollenauer |
| 2003/0208186 | A1 | 11/2003 | Moreyra |
| 2006/0022015 | A1 | 2/2006 | Shelton et al. |
| 2006/0025811 | A1 | 2/2006 | Shelton |
| 2007/0233052 | A1 | 10/2007 | Brock |
| 2007/0282358 | A1 | 12/2007 | Remiszewski et al. |
| 2008/0015631 | A1 | 1/2008 | Lee et al. |
| 2010/0274265 | A1 | 10/2010 | Wingardner et al. |
| 2010/0292691 | A1 | 11/2010 | Brogna |
| 2011/0118707 | A1 | 5/2011 | Burbank |
| 2011/0118708 | A1 | 5/2011 | Burbank et al. |
| 2011/0118709 | A1 | 5/2011 | Burbank |
| 2011/0118754 | A1 | 5/2011 | Dachs, II et al. |
| 2016/0066982 | A1* | 3/2016 | Marczyk ................ A61B 17/29 606/51 |

OTHER PUBLICATIONS

Extended European Search Report issued in corresponding European Application No. 20157439.9 dated Jun. 25, 2020, 9 pages.

* cited by examiner

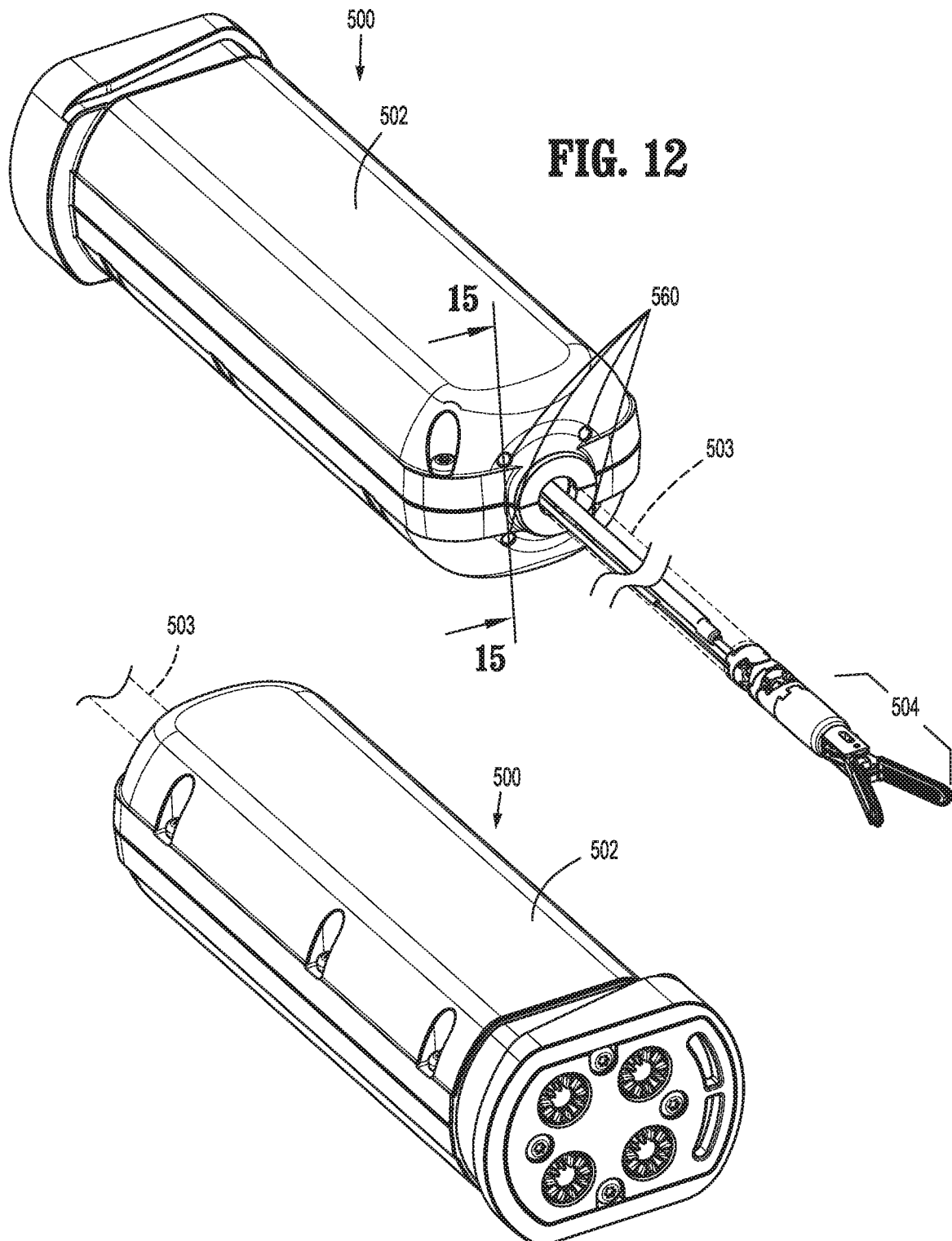

ARTICULATION MECHANISMS FOR SURGICAL INSTRUMENTS SUCH AS FOR USE IN ROBOTIC SURGICAL SYSTEMS

BACKGROUND

Technical Field

The present disclosure relates to surgical instruments and, more specifically, to articulation mechanisms for surgical instruments such as, for example, for use in robotic surgical systems.

Background of Related Art

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The number, type, and configuration of inputs provided by the robotic arm of a robotic surgical system are constraints in the design of surgical instruments configured for use with the robotic surgical system. That is, in designing a surgical instrument compatible for mounting on and use with the robotic arm of a robotic surgical system, consideration should be taken in determining how to utilize the available inputs provided by the robotic arm to achieve the desired functionality of the surgical instrument.

SUMMARY

As used herein, the term "distal" refers to the portion that is being described which is further from a surgeon, while the term "proximal" refers to the portion that is being described which is closer to a surgeon. The terms "about," "substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is an articulation assembly for a surgical instrument including first, second, third, and fourth proximal gear assemblies arranged such that the first and third proximal gear assemblies and the second and fourth proximal gear assemblies are diagonally-opposed relative to one another. The articulation assembly further includes first, second, third, and fourth distal gear assemblies coupled to the respective first, second, third, and fourth proximal gear assemblies and arranged such that the first and third distal gear assemblies and the second and fourth distal gear assemblies are diagonally-opposed relative to one another. The first and second distal gear assemblies are oppositely-configured relative to the third and fourth distal gear assemblies. A first coupling gear couples the first and third proximal gear assemblies such that an input to the first proximal gear assembly effects similar outputs from the first and third proximal gear assemblies to the first and third distal gear assemblies, respectively, which, in turn, provide opposite outputs due to the opposite configuration of the first and third distal gear assemblies. A second coupling gear couples the second and fourth proximal gear assemblies such that an input to the second proximal gear assembly effects similar outputs from the second and fourth proximal gear assemblies to the second and fourth distal gear assemblies, respectively, which, in turn, provide opposite outputs due to the opposite configuration of the second and fourth distal gear assemblies.

In an aspect of the present disclosure, each of the first, second, third, and fourth proximal gear assemblies includes a gear shaft defining an output, and a spur gear engaged about the gear shaft. In such aspects, the first coupling gear is disposed in meshed engagement with the spur gear of the first and third proximal gear assemblies and the second coupling gear is disposed in meshed engagement with the spur gear of the second and fourth proximal gear assemblies.

In another aspect of the present disclosure, a first gear set operably couples the first and third proximal gear assemblies with the first coupling gear. The first gear set is configured to amplify or attenuate the outputs from the first and third proximal gear assemblies relative to the input to the first proximal gear assembly. Additionally or alternatively, a second gear set operably couples the second and fourth proximal gear assemblies with the second coupling gear. The second gear set is configured to amplify or attenuate the outputs from the second and fourth proximal gear assemblies relative to the input to the second proximal gear assembly.

In still another aspect of the present disclosure, each of the first, second, third, and fourth distal gear assemblies includes a lead screw and a collar operably engaged about the lead screw such that rotation of the lead screw translates the collar to provide the output.

In yet another aspect of the present disclosure, the lead screws of the first and second lead screw assemblies define a first thread-pitch and the lead screws of the third and fourth lead screw assemblies define a second thread-pitch opposite the first thread-pitch, thereby defining the opposite configurations of the first and third distal gear assemblies and the opposite configurations of the second and fourth distal gear assemblies.

In still yet another aspect of the present disclosure, the articulation assembly further includes a proximal base assembly, an intermediate base assembly, and a distal base assembly. In such aspects, the first, second, third, and fourth proximal gear assemblies extend between the proximal and intermediate base assemblies, and the first, second, third, and fourth distal gear assemblies extend between the intermediate and distal base assemblies.

In another aspect of the present disclosure, the articulation assembly further includes first, second, third, and fourth articulation cables coupled to the outputs of the respective first, second, third, and fourth distal gear assemblies.

A surgical instrument provided in accordance with the present disclosure includes a housing, a shaft extending distally from the housing and including an articulating section, an end effector assembly extending distally from the shaft, and an articulation assembly disposed within the housing. The articulation assembly is configured to articulate the end effector assembly relative to the housing via first, second, third, and fourth articulation cables extending through the shaft. The articulation assembly may include the aspects and features of any of the articulation assemblies detailed above or otherwise detailed herein and is configured such that the outputs of the first, second, third and fourth distal gear assemblies are coupled to the first, second, third, and fourth articulation cables, respectively. In aspects, the end effector assembly includes first and second jaw members. At least the first jaw member is movable relative to the second jaw member from a spaced-apart position to an approximated position to grasp tissue therebetween.

A robotic surgical system provided in accordance with the present disclosure includes a surgical robot including a robotic arm configured to provide first and second rotational outputs. The robotic surgical system further includes a surgical instrument releasably mountable on the robotic arm, the surgical instrument includes an articulation assembly and may include any of the aspects and features of the surgical instruments detailed above or otherwise herein. The articulation assembly is configured to receive the first and second rotational outputs from the robotic arm and provide outputs coupled to the articulation cables for selectively articulating the end effector assembly.

Another articulation assembly provided in accordance with aspects of the present disclosure includes first, second, third, and fourth lead screw assemblies each including a lead screw and a collar operably engaged about the lead screw such that rotation of the lead screw translates the collar about the lead screw. The articulation assembly further includes first, second, third and fourth articulation cables operably coupled to the collars of the first, second, third, and fourth lead screw assemblies, respectively, such that proximal movement of one of the collars about the respective lead screw tensions the corresponding articulation cable and such that distal movement of one of the collars about the respective lead screw de-tensions the corresponding articulation cable. First, second, third and fourth proximal gear assemblies are coupled to the lead screws of the first, second, third, and fourth lead screw assemblies, respectively. A first coupling gear couples the first and third proximal gear assemblies with one another to maintain a pre-tension on the first and third articulation cables. A second coupling gear couples the second and fourth proximal gear assemblies with one another to maintain a pre-tension on the second and fourth articulation cables.

In an aspect of the present disclosure, the lead screws of the first and third lead screw assemblies define opposite thread-pitches relative to one another and the lead screws of the second and fourth lead screw assemblies define opposite thread-pitches relative to one another.

In another aspect of the present disclosure, the first coupling gear couples the first and third proximal gear assemblies such that the lead screws of the first and third lead screw assemblies are rotated in similar directions and, in aspects, such that the collars of the first and third lead screw assemblies are moved in opposite directions. The second coupling gear couples the second and fourth proximal gear assemblies such that the lead screws of the second and fourth lead screw assemblies are rotated in similar directions and, in aspects, such that the collars of the second and fourth lead screw assemblies are moved in opposite directions.

In yet another aspect of the present disclosure, the articulation assembly further includes a proximal base assembly, an intermediate base assembly, and a distal base assembly. The first, second, third, and fourth proximal gear assemblies extend between the proximal and intermediate base assemblies, and the first, second, third, and fourth distal gear assemblies extend between the intermediate and distal base assemblies.

In still another aspect of the present disclosure, each of the first, second, third, and fourth proximal gear assemblies includes a gear shaft defining an output configured to drive rotation of the corresponding lead screw, and a spur gear engaged about the gear shaft. In such aspects, the first coupling gear is disposed in meshed engagement with the spur gear of the first and third proximal gear assemblies and the second coupling gear is disposed in meshed engagement with the spur gear of the second and fourth proximal gear assemblies.

In still yet another aspect of the present disclosure, a first gear set operably couples the first and third proximal gear assemblies with the first coupling gear and is configured to amplify or attenuate the outputs from the first and third proximal gear assemblies to the corresponding lead screws relative to the input to the first proximal gear assembly. A second gear set operably couples the second and fourth proximal gear assemblies with the second coupling gear and is configured to amplify or attenuate the outputs from the second and fourth proximal gear assemblies to the corresponding lead screws relative to the input to the second proximal gear assembly.

A surgical instrument including the articulation assembly according to any of the above aspects and a robotic surgical system including the surgical instrument are also provided in accordance with aspects of the present disclosure.

Another articulation assembly for a surgical instrument provided in accordance with aspects of the present disclosure includes a first base assembly, a second base assembly, a first lead screw assembly, a first articulation cable, and a first set screw. The first lead screw assembly extends between the first and second base assemblies and includes a first lead screw and a first collar operably engaged about the first lead screw such that rotation of the first lead screw translates the first collar about the first lead screw. The first lead screw defines a proximal input end and a distal dock end. The proximal input end is rotatably received within the first base assembly and the distal dock end is rotatably received within the second base assembly. The first articulation cable is operably coupled to the first collar such that proximal movement of the first collar about the first lead screw tensions the first articulation cable and such that distal movement of the first collar about the first lead screw de-tensions the first articulation cable. The first set screw is threadingly engaged within the second base assembly and operably coupled to the distal dock end of the first lead screw such that proximal rotational driving of the first set screw relative to the second base assembly urges the first lead screw proximally, thereby urging the first collar proximally to increase tension on the first articulation cable.

In an aspect of the present disclosure, the second base assembly includes at least one first bushing that receives the distal dock end of the first lead screw. In such aspects, proximal rotational driving of the first set screw urges the first set screw into contact with the first bushing to thereby urge the first lead screw proximally.

In another aspect of the present disclosure, the first set screw is operably engaged within a first internally-threaded nut disposed within the second base assembly.

In still another aspect of the present disclosure, the articulation assembly includes a second lead screw assembly extending between the first and second base assemblies, a second articulation cable, and a second set screw. The second lead screw assembly includes a second lead screw and a second collar operably engaged about the second lead screw such that rotation of the second lead screw translates the second collar about the second lead screw. The second lead screw defines a proximal input end and a distal dock end. The proximal input end is rotatably received within the second base assembly and the distal dock end is rotatably received within the second base assembly. The second articulation cable is operably coupled to the second collar such that proximal movement of the second collar about the second lead screw tensions the second articulation cable and such that distal movement of the second collar about the second lead screw de-tensions the second articulation cable. The second set screw is threadingly engaged within the second base assembly and operably coupled to the distal dock end of the second lead screw such that proximal rotational driving of the second set screw relative to the second base assembly urges the second lead screw proximally, thereby urging the second collar proximally to increase tension on the second articulation cable.

In yet another aspect of the present disclosure, the articulation assembly further includes a first proximal gear assembly operably coupled to the proximal input end of the first lead screw assembly. The first proximal gear assembly is configured to drive rotation of the first lead screw to thereby translate the first collar along the first lead screw to tension or de-tension the first articulation cable.

In still yet another aspect of the present disclosure, the articulation assembly further includes a third base assembly. In such aspects, the first proximal gear assembly extends between the first and third base assemblies.

In another aspect of the present disclosure, the first proximal gear assembly includes a first gear shaft including an input end configured to receive an input and an output end configured to drive rotation of the first lead screw according to the input received at the input end.

In another aspect of the present disclosure, the first proximal gear assembly includes a first gear set configured to amplify or attenuate the output from the first proximal gear assemblies to the first lead screw assembly relative to an input to the first proximal gear assembly.

Another surgical instrument including the articulation assembly according to any of the above aspects and a robotic surgical system including the surgical instrument are also provided in accordance with aspects of the present disclosure. In aspects, the end effector assembly of the surgical instrument includes first and second jaw members. At least the first jaw member is movable relative to the second jaw member from a spaced-apart position to an approximated position to grasp tissue therebetween.

BRIEF DESCRIPTION OF THE DRAWINGS

Various aspects and features of the present disclosure are described hereinbelow with reference to the drawings wherein like numerals designate identical or corresponding elements in each of the several views.

FIG. 12 is a front, perspective view of another surgical instrument provided in accordance with the present disclosure configured for mounting on a robotic arm of a robotic surgical system;

FIG. 13 is a rear, perspective view of a proximal portion of the surgical instrument of FIG. 12;

DETAILED DESCRIPTION

Figure 1A:
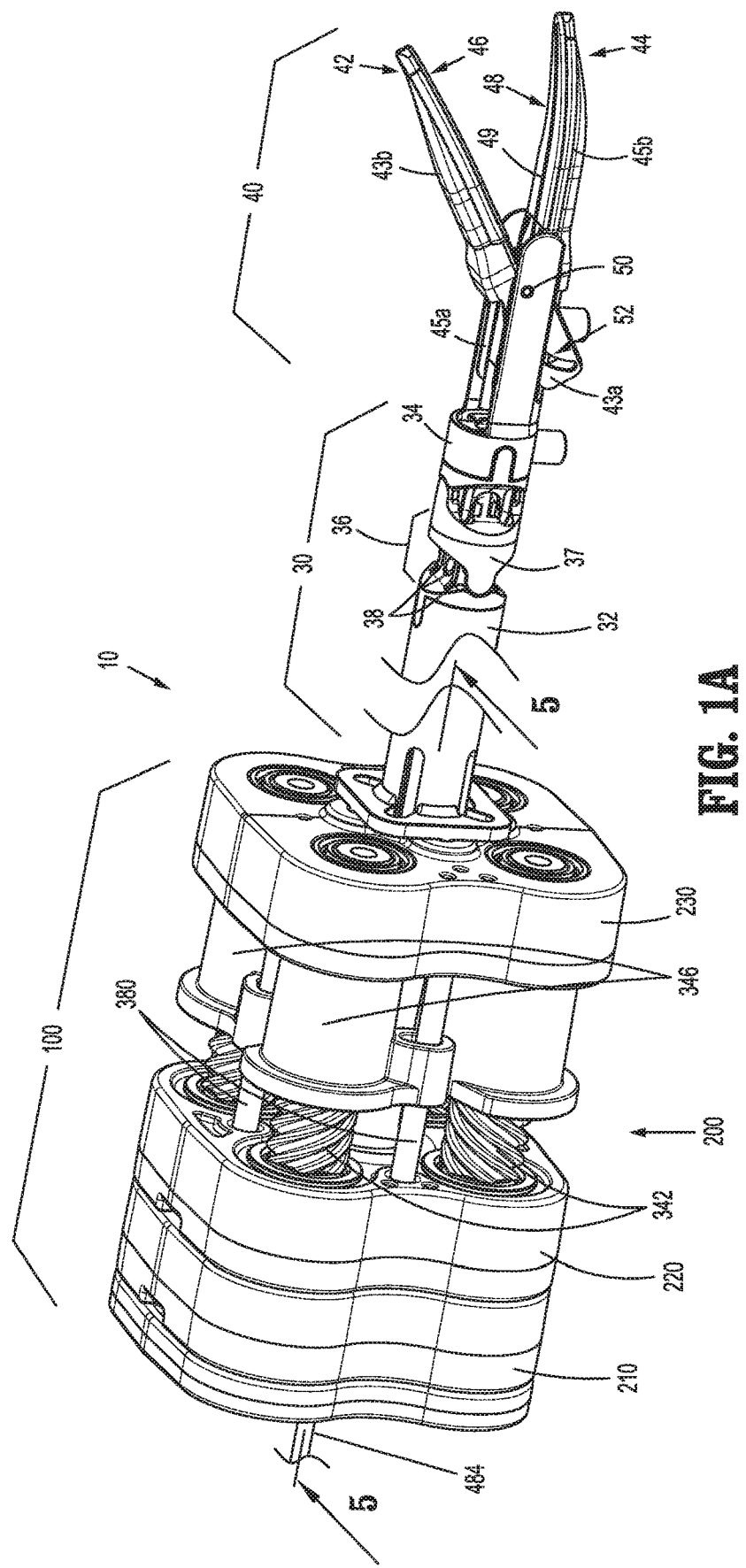
FIG. 1A is a perspective view of an articulation assembly, shaft, and end effector assembly of a surgical instrument provided in accordance with the present disclosure configured for mounting on a robotic arm of a robotic surgical system.
Figure 1B:
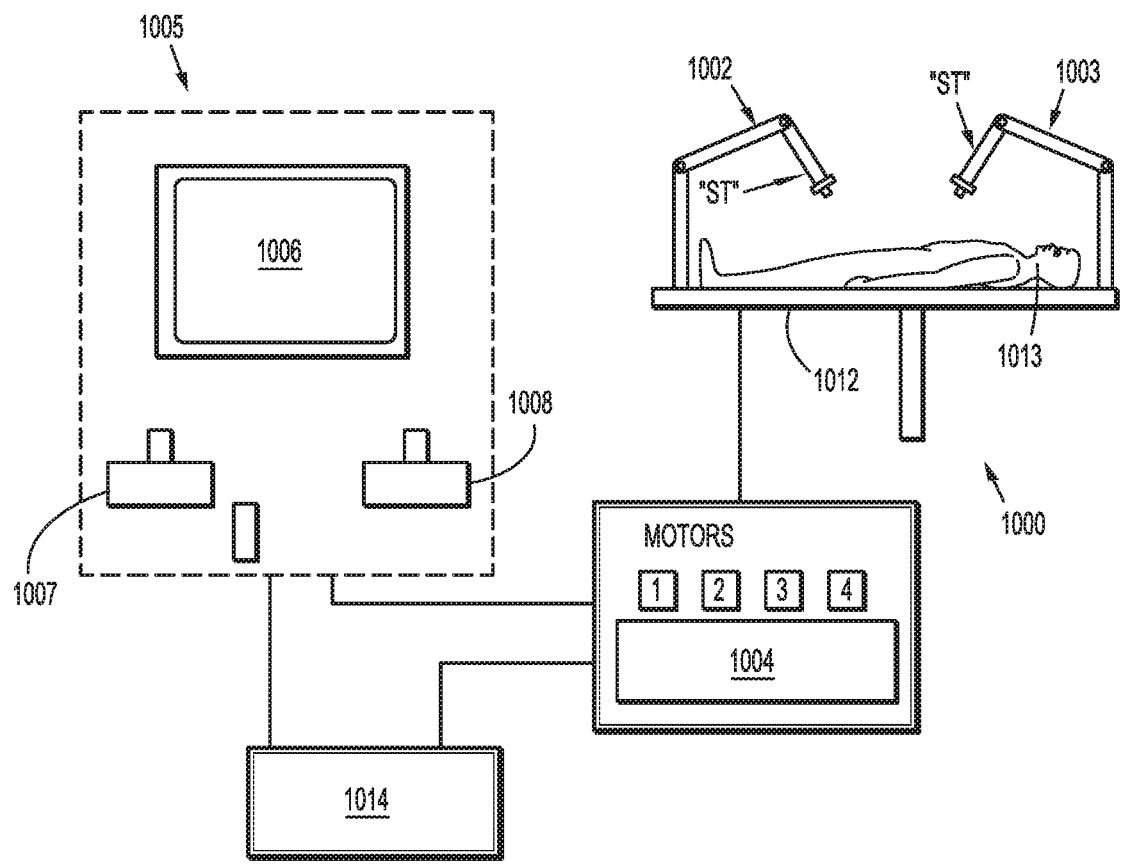
FIG. 1B is a schematic illustration of an exemplary robotic surgical system configured to releasably receive the surgical instrument of FIG. 1A.
Figure 2:
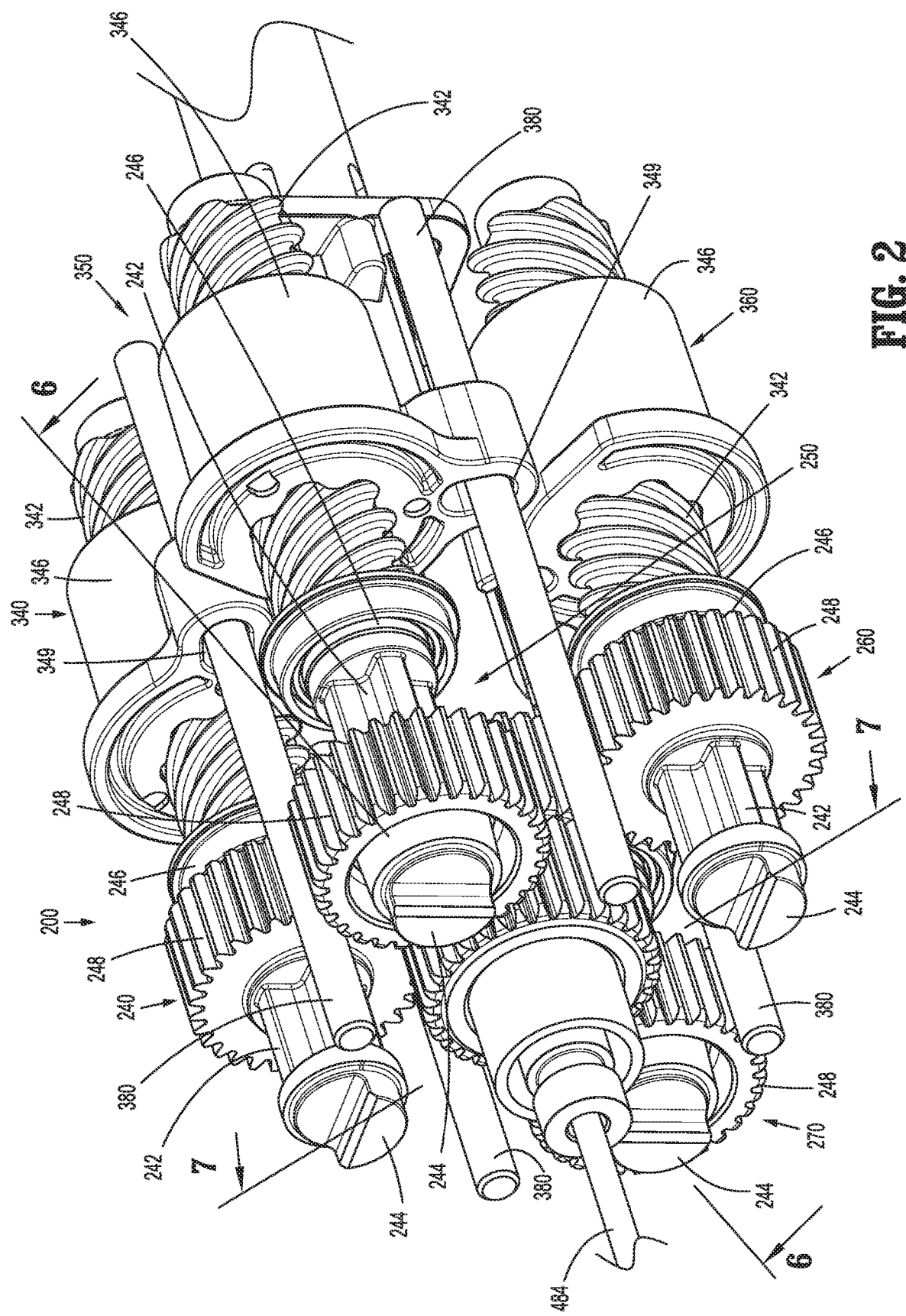
FIG. 2 is a rear, perspective view of the articulation assembly of the surgical instrument of FIG. 1A, with portions removed.

Referring to FIG. 1A, a surgical instrument 10 provided in accordance with the present disclosure generally includes a housing (not shown; similar to housing 502 of surgical instrument 500 (FIGS. 12-16)), a shaft 30 extending distally from the housing, an end effector assembly 40 extending distally from shaft 30, and a gearbox assembly 100 disposed within the housing and operably associated with end effector assembly 40. Instrument 10 is detailed herein as an articulating electrosurgical forceps configured for use with a robotic surgical system, e.g., robotic surgical system 1000 (FIG. 1B). However, the aspects and features of instrument 10 provided in accordance with the present disclosure, detailed below, are equally applicable for use with other suitable surgical instruments and/or in other suitable surgical systems.

Shaft 30 of instrument 10 includes a proximal segment 32, a distal segment 34, and an articulating section 36 disposed between the proximal and distal segments 32, 34, respectively. Articulating section 36 includes one or more articulating components 37, e.g., links, joints, etc. A plurality of articulation cables 38 (see also FIG. 3), e.g., four (4) articulation cables, or other suitable actuators, extend through articulating section 36. More specifically, articulation cables 38 are operably coupled to distal segment 34 of shaft 30 at the distal ends thereof and extend proximally from distal segment 34 of shaft 30, through articulating section 36 of shaft 30 and proximal segment 32 of shaft 30, and into the housing, wherein articulation cables 38 operably couple with articulation sub-assembly 200 of gearbox assembly 100 to enable selective articulation of distal segment 34 (and, thus end effector assembly 40) relative to proximal segment 32 and the housing, e.g., about at least two axes of articulation (yaw and pitch articulation, for example). Articulation cables 38 are arranged to define a generally square configuration, although other suitable configurations are also contemplated.

With respect to articulation of end effector assembly 40 relative to proximal segment 32 of shaft 30, actuation of articulation cables 38 is effected in pairs. More specifically, in order to pitch end effector assembly 40, the upper pair of articulation cables 38 are actuated in a similar manner while the lower pair of articulation cables 38 are actuated in a similar manner relative to one another but an opposite manner relative to the upper pair of articulation cables 38 (see also FIG. 3). With respect to yaw articulation, the right pair of articulation cables 38 are actuated in a similar manner while the left pair of articulation cables 38 are actuated in a similar manner relative to one another but an opposite manner relative to the right pair of articulation cables 38 (see also FIG. 3).

Continuing with reference to FIG. 1A, end effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 34 of shaft 30 between a spaced-apart position (e.g., an open position of end effector assembly 40) and an approximated position (e.g., a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 34 of shaft 30.

In embodiments, longitudinally-extending knife channels 49 (only knife channel 49 of jaw member 44 is illustrated; the knife channel of jaw member 42 is similarly configured) are defined through tissue-contacting surfaces 46, 48, respectively, of jaw members 42, 44. In such embodiments, a knife assembly (not shown) including a knife tube (not shown) extending from the housing through shaft 30 to end effector assembly 40 and a knife blade (not shown) disposed within end effector assembly 40 between jaw members 42, 44 is provided to enable cutting of tissue grasped between tissue-contacting surfaces 46, 48 of jaw members 42, 44, respectively. The knife tube is operably coupled to a knife drive sub-assembly (not shown) of gearbox assembly 100 at a proximal end thereof to enable selective actuation to, in turn, reciprocate the knife blade between jaw members 42, 44 to cut tissue grasped between tissue-contacting surfaces 46, 48.

Referring still to FIG. 1A, a drive rod 484 is operably coupled to cam-slot assembly 52 of end effector assembly 40, e.g., engaged with the cam pin thereof, such that longitudinal actuation of drive rod 484 pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into the housing wherein drive rod 484 is operably coupled with a jaw drive sub-assembly (not shown) of gearbox assembly 100 to enable selective actuation of end effector assembly 40 to grasp tissue therebetween and apply a closure force within an appropriate jaw closure force range.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, ultrasound, etc., through tissue grasped therebetween for energy-based tissue treatment. Instrument 10 defines a conductive pathway (not shown) through the housing and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator, for supplying energy to tissue-contacting surfaces 46, 48 to treat, e.g., seal, tissue grasped between tissue-contacting surfaces 46, 48.

Gearbox assembly 100 is disposed within the housing and, as noted above, includes an articulation sub-assembly 200, a knife drive sub-assembly (not shown), and a jaw drive sub-assembly (not shown). Articulation sub-assembly 200, as detailed below, is operably coupled between first and second rotational inputs, respectively, provided to gearbox assembly 100, and articulation cables 38 such that, upon receipt of appropriate inputs into the first and/or second rotational inputs, articulation sub-assembly 200 manipulates articulation cables 38 to articulate end effector assembly 40 in a desired direction, e.g., to pitch and/or yaw end effector assembly 40.

The knife drive sub-assembly is operably coupled between a third rotational input provided to gearbox assembly 100 such that, upon receipt of appropriate input into the third rotational input, the knife drive sub-assembly manipulates the knife tube to reciprocate the knife blade between jaw members 42, 44 to cut tissue grasped between tissue-contacting surfaces 46, 48.

The jaw drive sub-assembly is operably coupled between a fourth rotational input provided to gearbox assembly 100 and drive rod 484 such that, upon receipt of appropriate input into the fourth rotational input, the jaw drive sub-assembly pivots jaw members 42, 44 between the spaced-apart and approximated positions to grasp tissue therebetween and apply a closure force within an appropriate closure force range.

Gearbox assembly 100 is configured to operably interface with a robotic surgical system 1000 (FIG. 1B) when instrument 10 is mounted on robotic surgical system 1000 (FIG. 1B), to enable robotic operation of gearbox assembly 100 to provide the above-detailed functionality, e.g., to provide the rotational inputs to gearbox assembly 100. However, it is also contemplated that gearbox assembly 100 be configured to interface with any other suitable surgical system, e.g., a manual surgical handle, a powered surgical handle, etc. For the purposes herein, robotic surgical system 1000 (FIG. 1B) is generally described.

Turning to FIG. 1B, robotic surgical system 1000 is configured for use in accordance with the present disclosure.

Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and mounted device which may be, for example, a surgical tool "ST." One or more of the surgical tools "ST" may be instrument 10 (FIG. 1A), thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

With reference to FIGS. 2-7, articulation sub-assembly 200 of gearbox assembly 100 is shown generally including a proximal base assembly 210, an intermediate base assembly 220, a distal base assembly 230, four proximal gear assemblies 240, 250, 260, 270, two coupling gears 280, 290 four distal gear assemblies configured as lead screw assemblies 340, 350, 360, 370 (although other suitable distal gear assemblies are also contemplated), and four guide dowels 380. As an alternative or in addition to coupling gears 280, 290, belts may be utilized to provide the coupling. Likewise, other gearing components detailed herein may be replaced or supplemented with the use of belts instead of directly meshed gears, without departing from the present disclosure. Further, in embodiments, multiple gears (and/or belts) may be provided in place of single gears (and/or belts) to provide a desired amplification or attenuation effect.

Each of the proximal, intermediate, and distal base assemblies 210, 220, 230, respectively, includes a base plate 212, 222, 232 defining four apertures 214, 224, 234 arranged in a generally square configuration. Bushings 216, 226, 236 are engaged within the apertures 214, 224, 234 of each of proximal, intermediate, and distal base assemblies 210, 220, 230, respectively.

Each proximal gear assembly 240, 250, 260, 270 includes a gear shaft 242 defining an input 244 at a proximal end thereof. However, only two inputs 244 are needed and, indeed, only two are utilized, as detailed below. Thus, in some embodiments, only two of the proximal gear assemblies, e.g., proximal gear assemblies 240, 250, include inputs 244 while the other two proximal gear assemblies, e.g., proximal gear assemblies 260, 270, do not. Each proximal gear assembly 240, 250, 260, 270 further includes an output 246 at a distal end thereof. A spur gear 248 is mounted on the respective gear shaft 242 of each proximal gear assembly 240, 250, 260, 270. Proximal gear assemblies 240, 250, 260, 270 are arranged to define a generally square configuration such that the spur gear 248 of each proximal gear assembly 240, 250, 260, 270, includes two adjacent spur gears 248, e.g., a vertically-adjacent spur gear 248 and a horizontally-adjacent spur gear 248, and a diagonally-opposed spur gear 248. One pair of diagonally-opposed spur gears 248, e.g., spur gears 248 of proximal gear assemblies 240, 260, are longitudinally offset relative to the other pair of diagonally-opposed spur gears 248, e.g., spur gears 248 of proximal gear assemblies 250, 270. More specifically, spur gears 248 of proximal gear assemblies 240, 260 are more-distally disposed as compared to spur gears 248 of proximal gear assemblies 250, 270.

The utilized inputs 244 (or inputs 244 provided, where only two are provided), e.g., the inputs 244 of proximal gear assemblies 240, 250, extend proximally into a corresponding bushing 216 disposed within an aperture 214 of base plate 212 of proximal base assembly 210. In this manner, the two inputs 244 are positioned at a proximal end of articulation sub-assembly 200 to receive two rotational inputs for articulation, e.g., from a robotic surgical system 1000 (FIG. 1B). The output 246 of each proximal gear assembly 240, 250, 260, 270 extends distally into a corresponding bushing 226 disposed within an aperture 224 of base plate 222 of intermediate base assembly 220. As detailed below, this enables the output 246 of each proximal gear assembly 240, 250, 260, 270 to provide a rotational output to a corresponding lead screw assembly 340, 350, 360, 370, respectively.

Continuing with reference to FIGS. 2-7, the two coupling gears 280, 290 operably couple the spur gears 248 of each diagonally-opposed pair of spur gears 248. More specifically, the more-distal coupling gear 280 is disposed in meshed engagement with the more-distally disposed spur gears 248 of proximal gear assemblies 240, 260, while the more-proximal coupling gear 290 is disposed in meshed engagement with the more-proximally disposed spur gears 248 of proximal gear assemblies 250, 270.

As a result of the above-detailed configuration, for example, a rotational input provided to input 244 of proximal gear assembly 240 rotates output 246 and spur gear 248 of proximal gear assembly 240 in a first direction to, in turn, rotate coupling gear 280 in a second, opposite direction which, in turn, rotates spur gear 248 and output 246 of proximal gear assembly 260 in the first direction. Further, as another example, a rotational input provided to input 244 of proximal gear assembly 250 rotates output 246 and spur gear 248 of proximal gear assembly 250 in a first direction to, in turn, rotate coupling gear 290 in a second, opposite direction which, in turn, rotates spur gear 248 and output 246 of proximal gear assembly 270 in the first direction. Thus, only two rotational inputs are required to provide a rotational output at the output 246 of each proximal gear assembly 240, 250, 260, 270: one to the input 244 of proximal gear assembly 240 or proximal gear assembly 260, and the other to the input 244 of proximal gear assembly 250 or proximal gear assembly 270. As noted above, only two inputs 244 thus need be provided, e.g., input 244 of proximal gear assembly 240 and input 244 of proximal gear assembly 250.

Each lead screw assembly 340, 350, 360, 370 includes a lead screw 342 defining a proximal input end 343 and a distal dock end 345. Each lead screw assembly 340, 350, 360, 370 further includes a collar 346 operably threadingly engaged about the corresponding lead screw 342 such that rotation of the lead screw 342 translates the corresponding collar 346 longitudinally therealong. The proximal input end 343 of the lead screw 342 of each lead screw assembly 340, 350, 360, 370 extends proximally into a corresponding bushing 226 disposed within an aperture 224 of base plate 222 of intermediate base assembly 220 wherein the proximal input end 343 is operably coupled with the output 246 of a corresponding proximal gear assembly 240, 250, 260, 270 such that rotation of outputs 246 effect corresponding rotation of lead screws 342. The distal dock end 345 of the lead screw 342 of each lead screw assembly 340, 350, 360, 370 extend distally into and is rotationally seated within a corresponding bushing 236 disposed within an aperture 234 of base plate 232 of distal base assembly 230.

Referring still to FIGS. 2-7, lead screw assemblies 340, 350, 360, 370, similarly as with proximal gear assemblies 240, 250, 260, 270, are arranged to define a generally square configuration such that the lead screw 342 of each lead screw assembly 340, 350, 360, 370, includes two adjacent lead screws 342, e.g., a vertically-adjacent lead screw 342 and a horizontally-adjacent lead screw 342, and a diagonally-opposed lead screw 342. The lead screws 342 of each diagonally-opposed pair of lead screws 342 define opposite thread-pitch directions. For example, lead screw 342 of lead screw assembly 340 may define a right-handed thread-pitch while the diagonally-opposite lead screw 342 of lead screw assembly 360 defines a left-handed thread-pitch. Similarly, lead screw 342 of lead screw assembly 350 may define a right-handed thread-pitch while the diagonally-opposite lead screw 342 of lead screw assembly 370 defines a left-handed thread-pitch.

As noted above, each collar 346 is operably threadingly engaged about a corresponding lead screw 342 such that rotation of the lead screw 342 translates the corresponding collar 346 longitudinally therealong. Each collar 346 includes a ferrule 348 configured to engage a proximal end portion of one of the articulation cables 38 (see FIG. 3), e.g., via a crimped hook-slot engagement or other suitable engagement (mechanical fastening, adhesion, welding, etc.). Thus, distal translation of a collar 346 slackens the corresponding articulation cable 38 by pushing the corresponding articulation cable 38 in a distal direction, while proximal translation of a collar 346 tensions the corresponding articulation cable 38 by pulling the corresponding articulation cable 38 in a proximal direction.

The four guide dowels 380 are engaged and extend between intermediate and distal base assemblies 320, 330, respectively, and are arranged in a generally square configuration. Each guide dowel 380 extends through a sleeve 349 of a collar 346 of a corresponding lead screw assembly 340, 350, 360, 370. Guide dowel 380 guide translation of collars 346 along lead screws 342 and inhibit rotation of collars 346 relative to lead screws 342.

Figure 3:
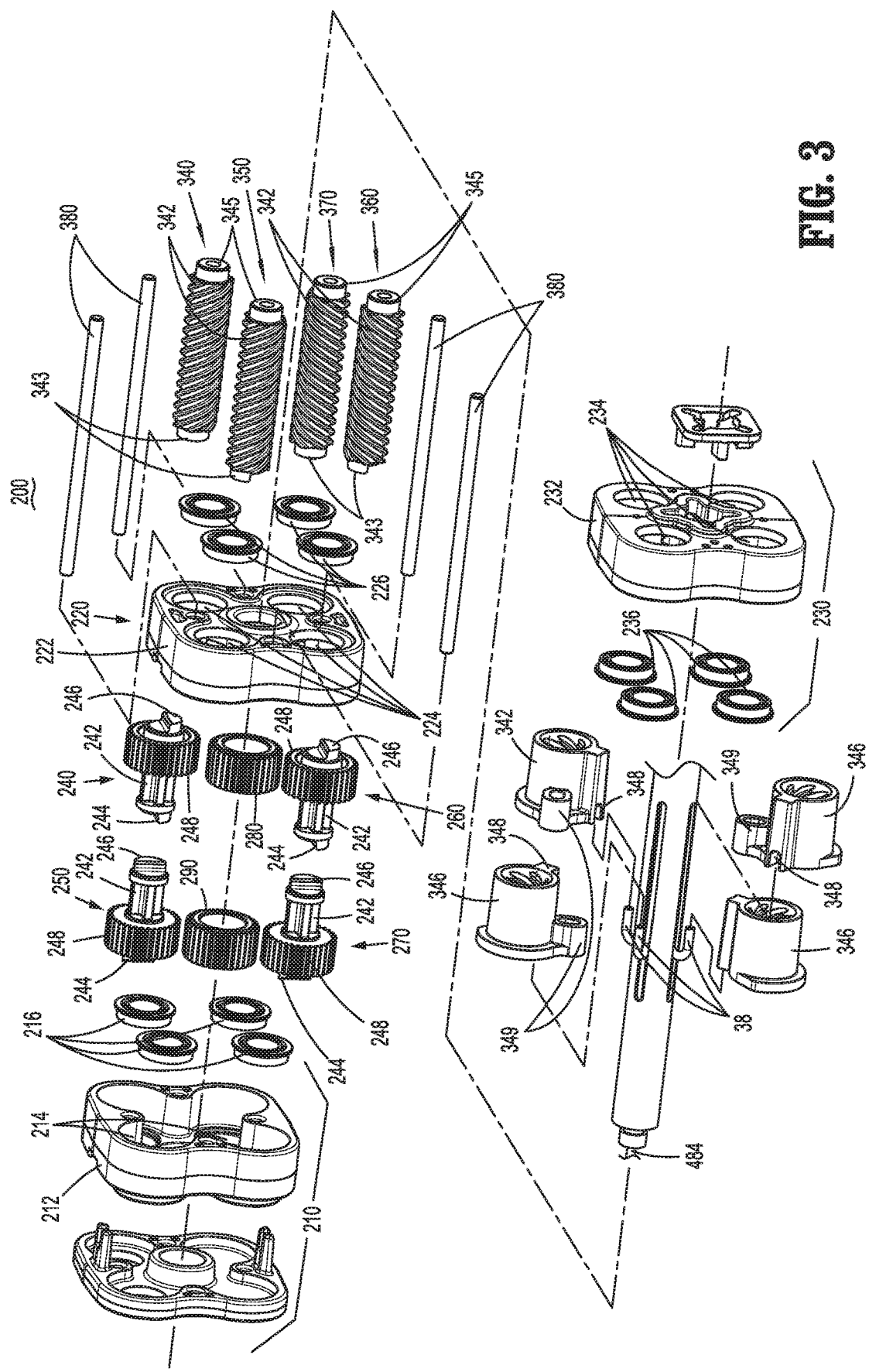
FIG. 3 is an exploded, perspective view of the articulation assembly of the surgical instrument of FIG. 1A.
Figure 4:
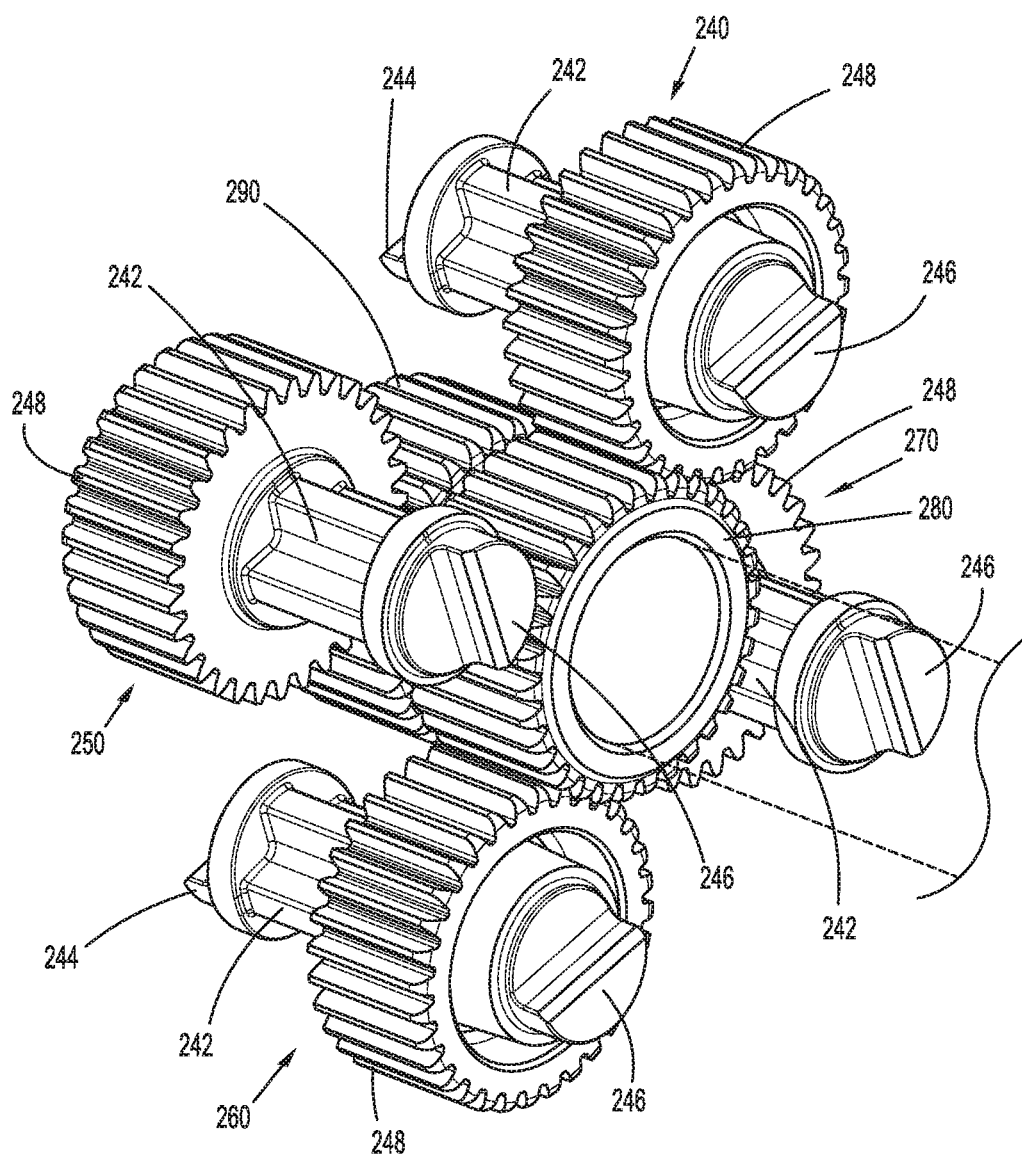
FIG. 4 is a side, perspective view of a proximal portion of the articulation assembly of FIG. 2.
Figure 5:
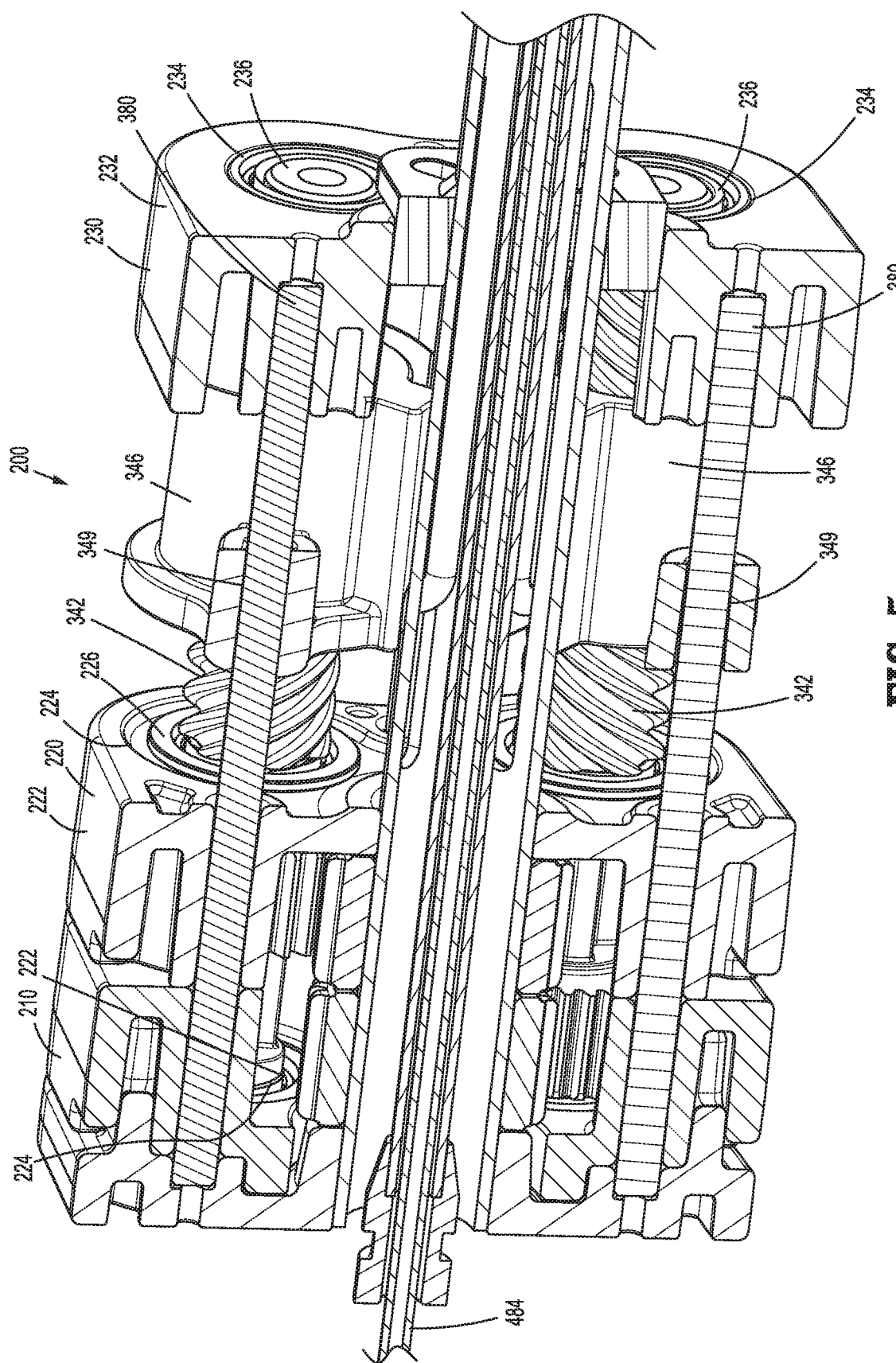
FIG. 5 is a longitudinal, cross-sectional view taken along section line "5-5" of FIG. 1A.
Figure 6:
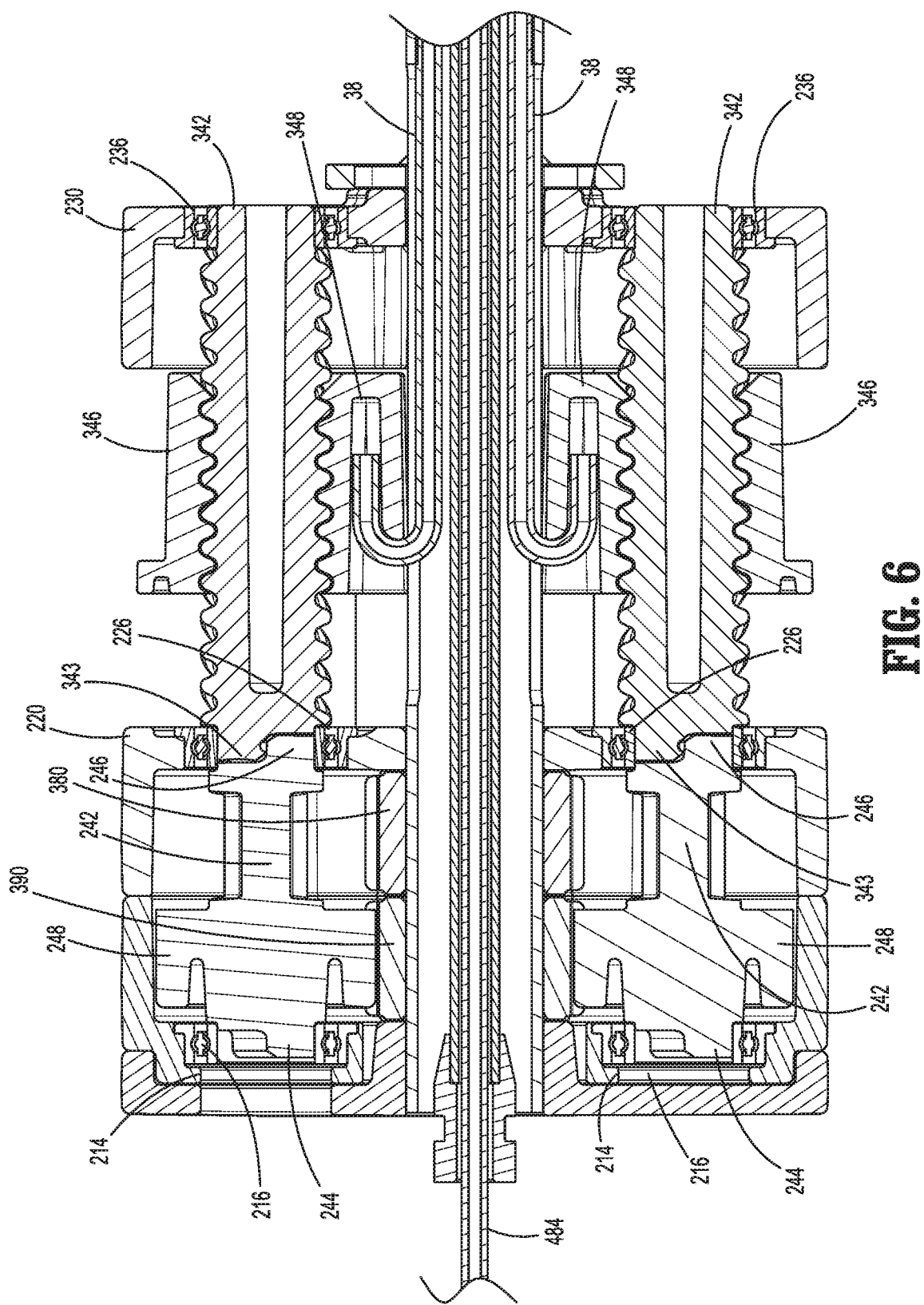
FIG. 6 is a transverse, cross-sectional view taken along section line "6-6" of FIG. 2.
Figure 7:
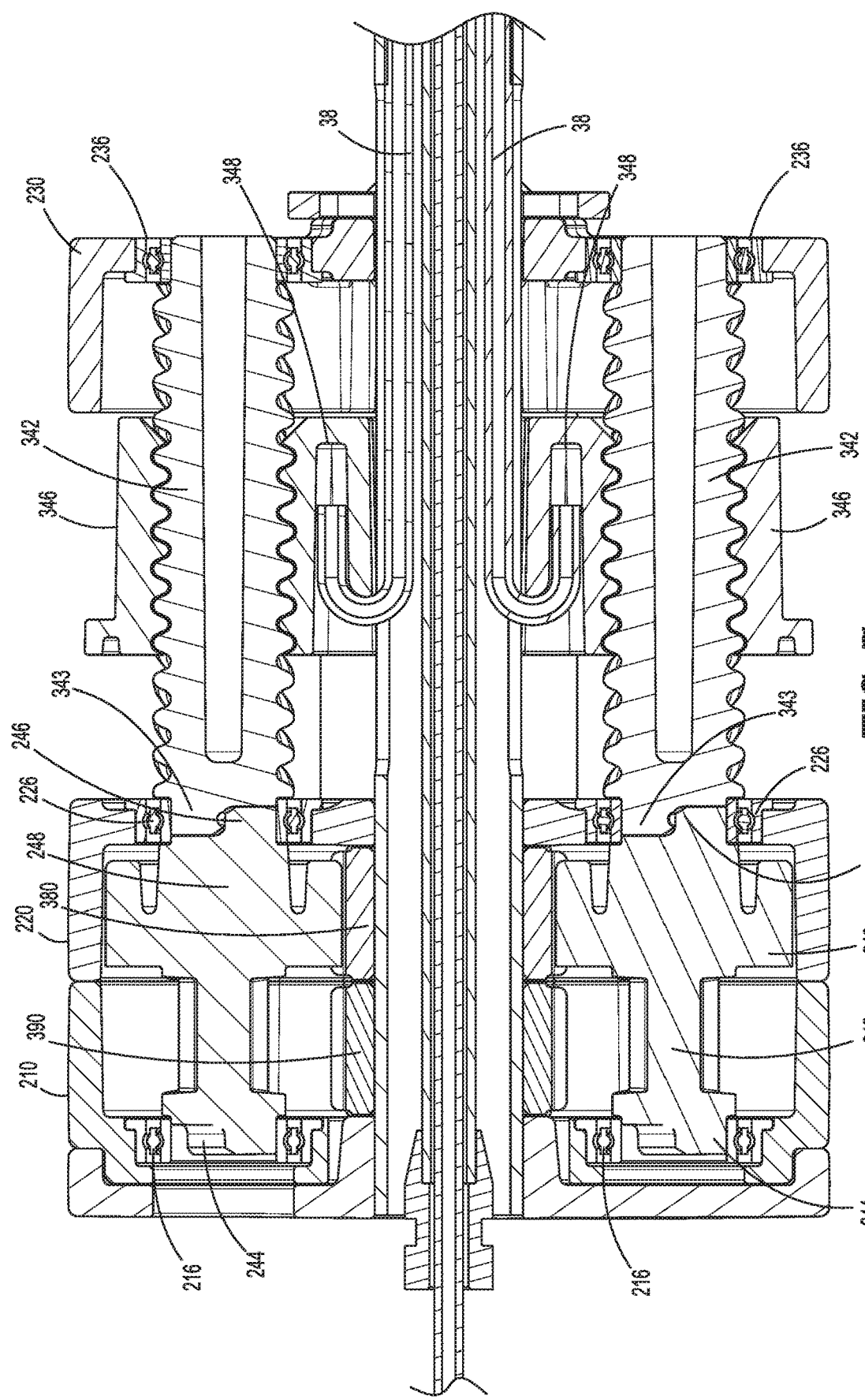
FIG. 7 is a transverse, cross-sectional view taken along section line "7-7" of FIG. 2.
Figure 8:
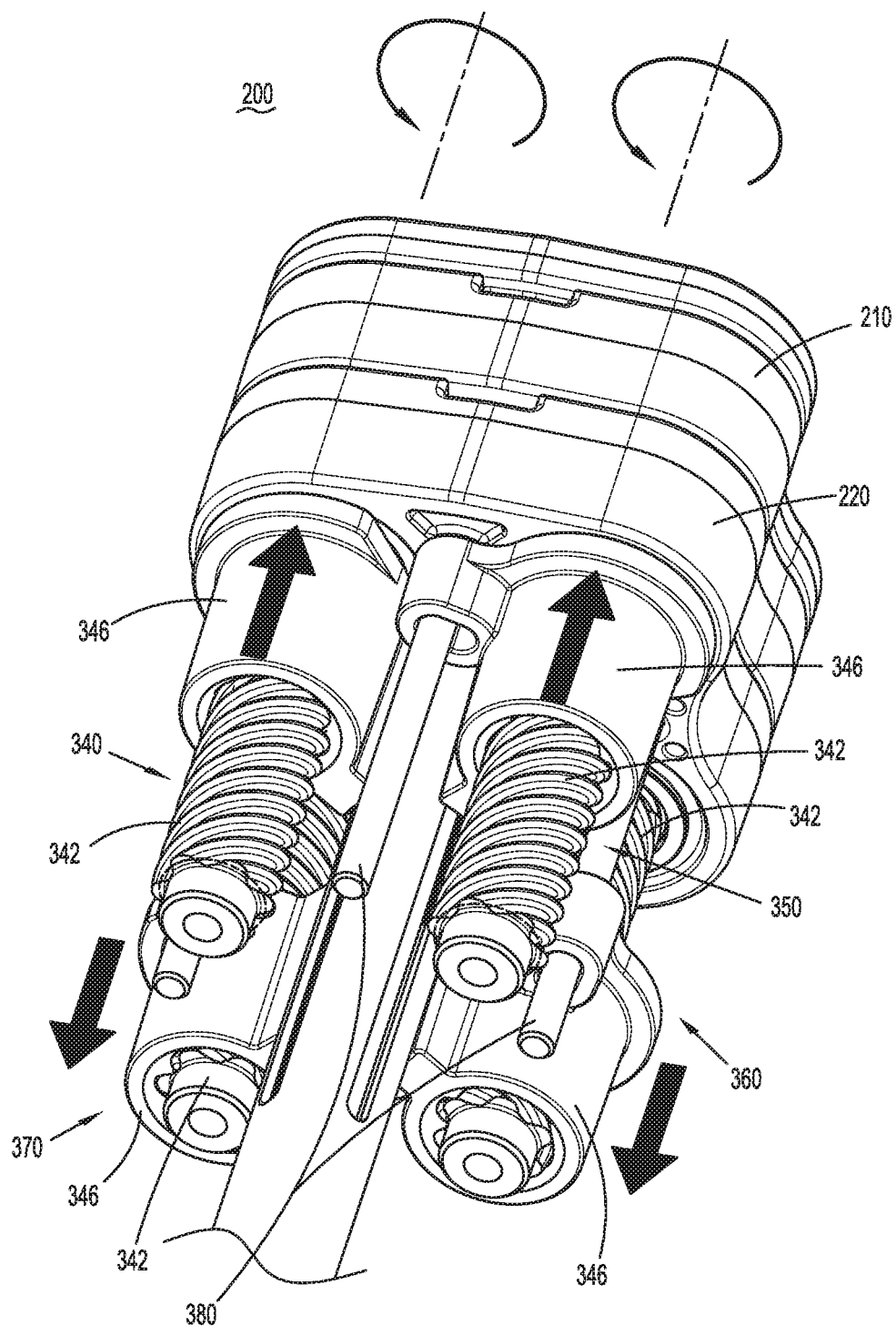
FIG. 8 is a top, front, perspective view of the articulation assembly of FIG. 2 with portions removed, illustrating actuation thereof in a first manner.
Figure 9:
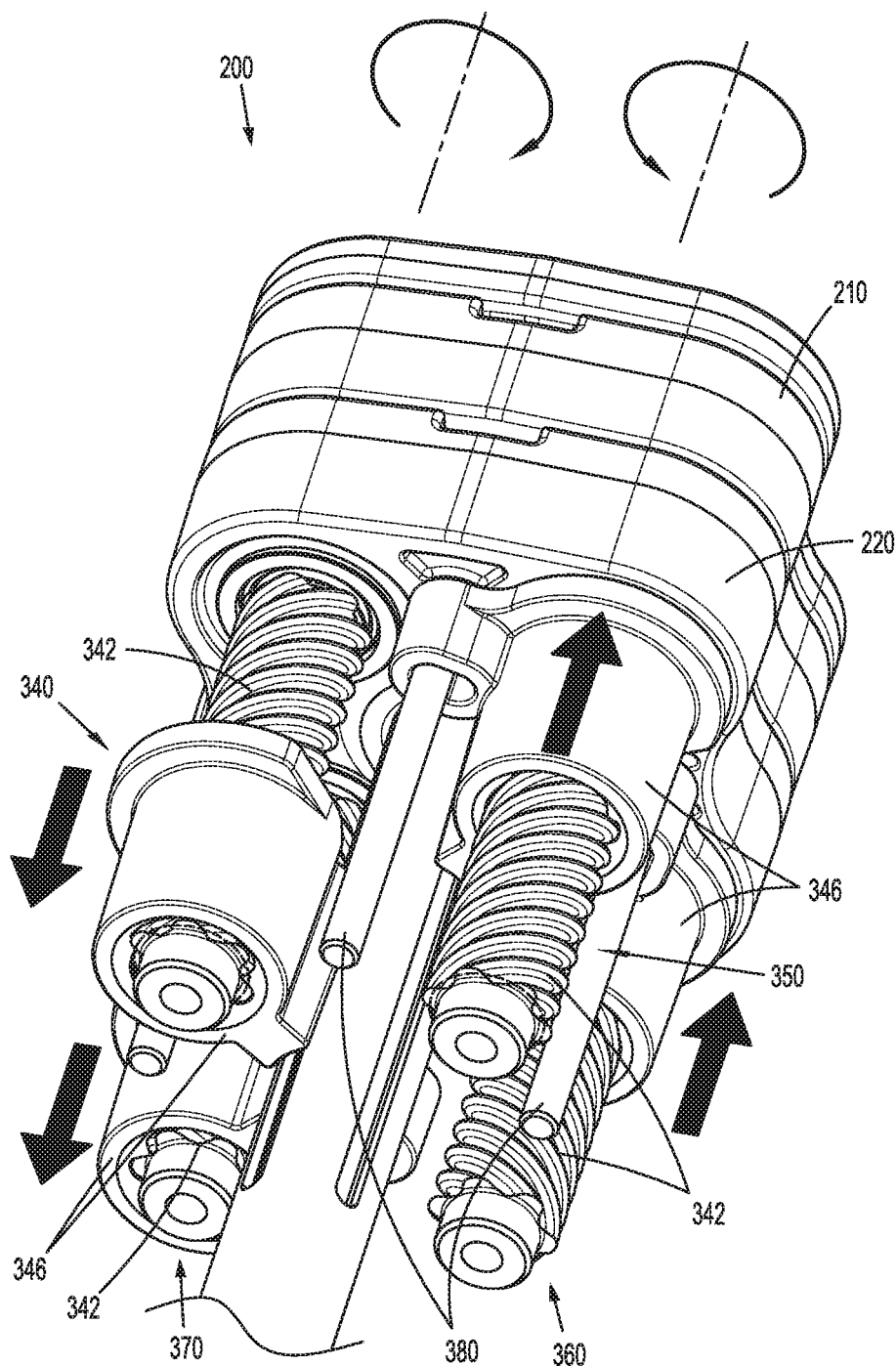
FIG. 9 is a top, front, perspective view of the articulation assembly of FIG. 2 with portions removed, illustrating actuation thereof in a second manner.

Turning to FIG. 8, in conjunction with FIG. 3, in order to pitch end effector assembly 40 (FIG. 1), collars 346 of lead screw assemblies 340, 350 are translated in a similar manner to actuate the upper pair of articulation cables 38 (FIG. 3) in a similar manner while collars 346 of lead screw assemblies 360, 370 are translated similarly to one another but opposite of the collars 346 of lead screw assemblies 340, 350 such that the lower pair of articulation cables 38 (FIG. 3) are actuated in a similar manner relative to one another but an opposite manner relative to the upper pair of articulation cables 38. Referring to FIG. 9, in conjunction with FIG. 3, with respect to yaw articulation of end effector assembly 40 (FIG. 1), collars 346 of lead screw assemblies 340, 370 are translated in a similar manner to actuate the right pair of articulation cables 38 (FIG. 3) in a similar manner while collars 346 of lead screw assemblies 350, 360 are translated similarly to one another but opposite of the collars 346 of lead screw assemblies 340, 370 such that the left pair of articulation cables 38 (FIG. 3) are actuated in a similar manner relative to one another but an opposite manner relative to the right pair of articulation cables 38.

With general reference to FIGS. 2-9, as demonstrated above, the collars 346 of opposing diagonal pairs of collars 346 always move in opposite directions relative to one another to effect articulation, regardless of whether of pitch and/or yaw articulation is desired and regardless of the direction of articulation, e.g., up pitch, down pitch, left yaw, right yaw, or combinations thereof. As also detailed above, a rotational input provided to input 244 of proximal gear assembly 240 or proximal gear assembly 260 provides a similar rotational output at the output 246 of both proximal gear assembly 240 and proximal gear assembly 260 due to the coupling thereof via coupling gear 280 and, thus, lead screw assemblies 340, 360 receive similar inputs from proximal gear assemblies 240, 260, respectively. However, since the thread-pitch of the lead screws 342 of lead screw assemblies 340, 360 are opposite one another, the similar inputs provided thereto effect opposite translation of the collars 346 thereof. Likewise, a rotational input provided to input 244 of proximal gear assembly 250 or proximal gear assembly 270 provides a similar rotational output at both outputs 246 due to the coupling thereof via coupling gear 290 and, thus, lead screw assemblies 350, 370 receive similar inputs from proximal gear assemblies 250, 270, respectively, to, in turn, effect opposite translation of the collars 346 thereof. Thus, by controlling the directions of two rotational inputs (one to the input 244 of proximal gear assembly 240 or proximal gear assembly 260, and the other to the input 244 of proximal gear assembly 250 or proximal gear assembly 270), pitch and/or yaw articulation in any suitable direction may be achieved.

Figure 10:
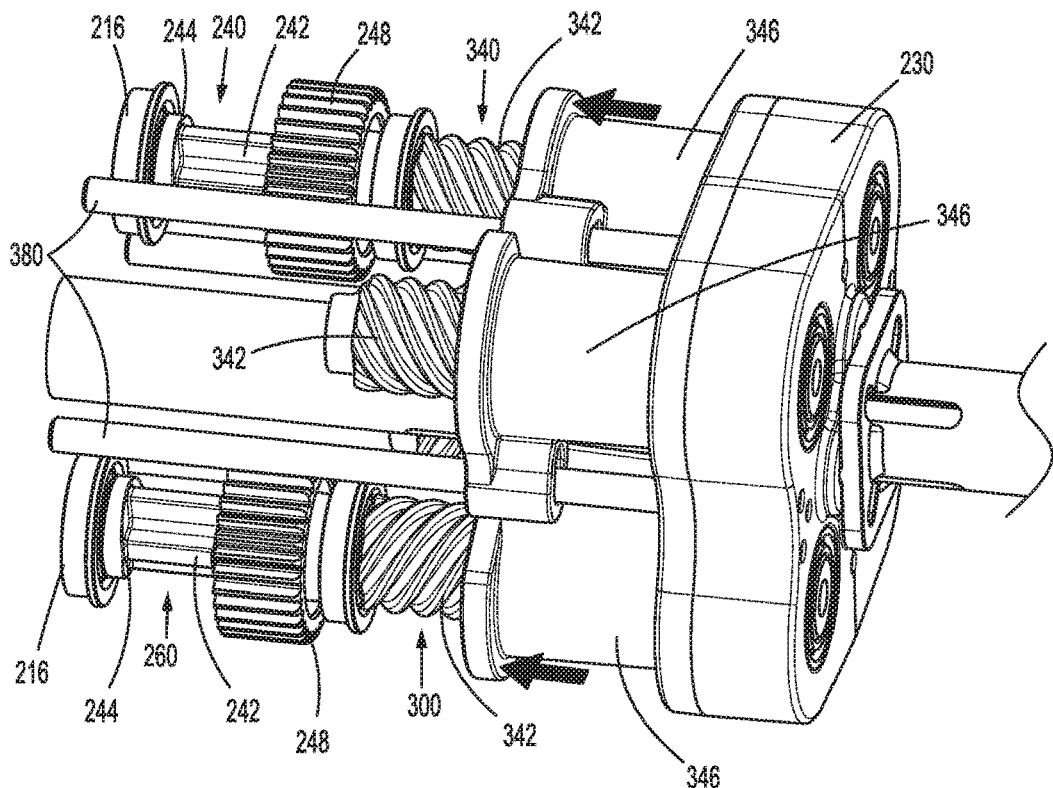
FIGS. 10 and 11 are side, perspective view of the articulation assembly of FIG. 2 with portions removed, illustrating pre-tensioning and assembly of the articulation assembly of the surgical instrument of FIG. 1A.
Figure 11:
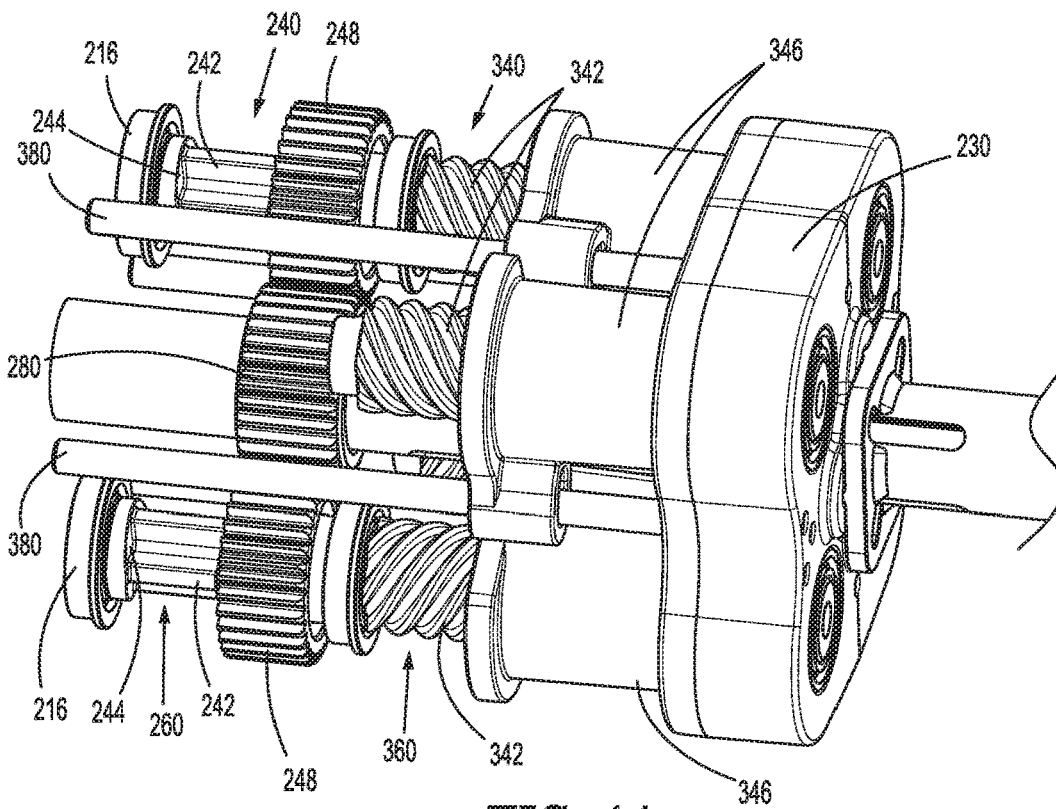
Figure 14:
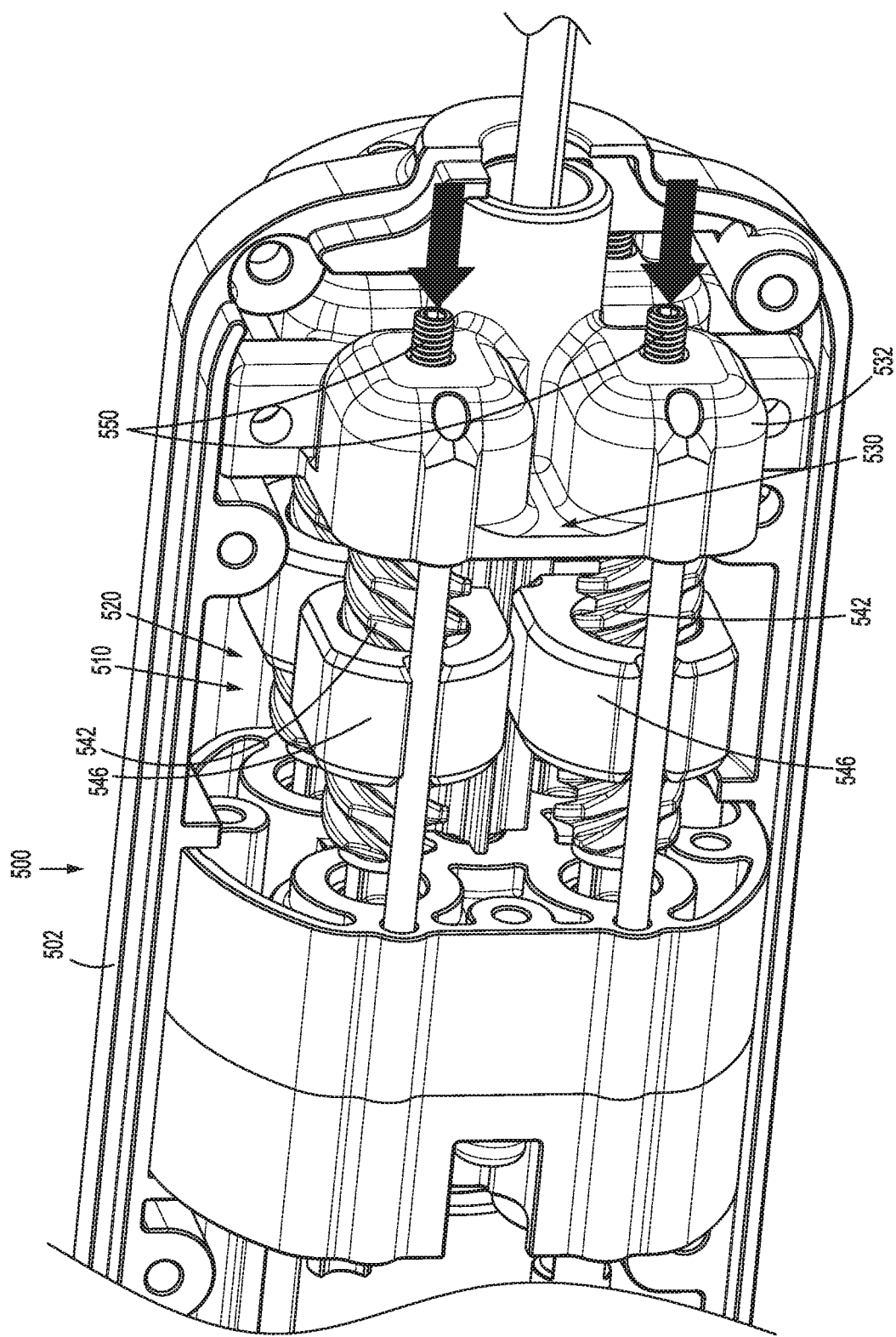
FIG. 14 is a side, perspective view of a portion the surgical instrument of FIG. 12 with an outer housing half removed to illustrate internal components therein.
Figure 15:
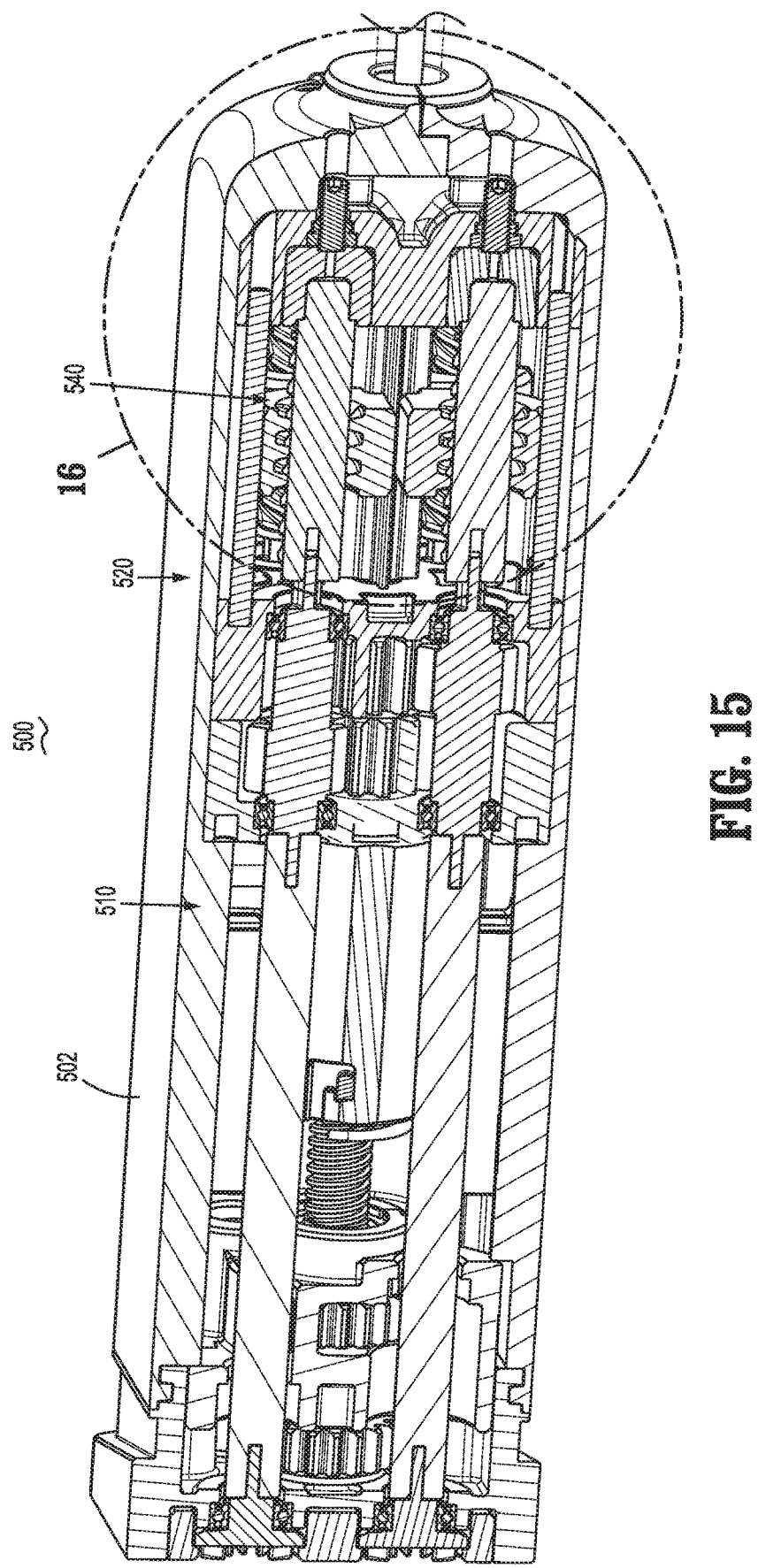
FIG. 15 is transverse, cross-sectional view taken along section line "15-15" of FIG. 12.
Figure 16:
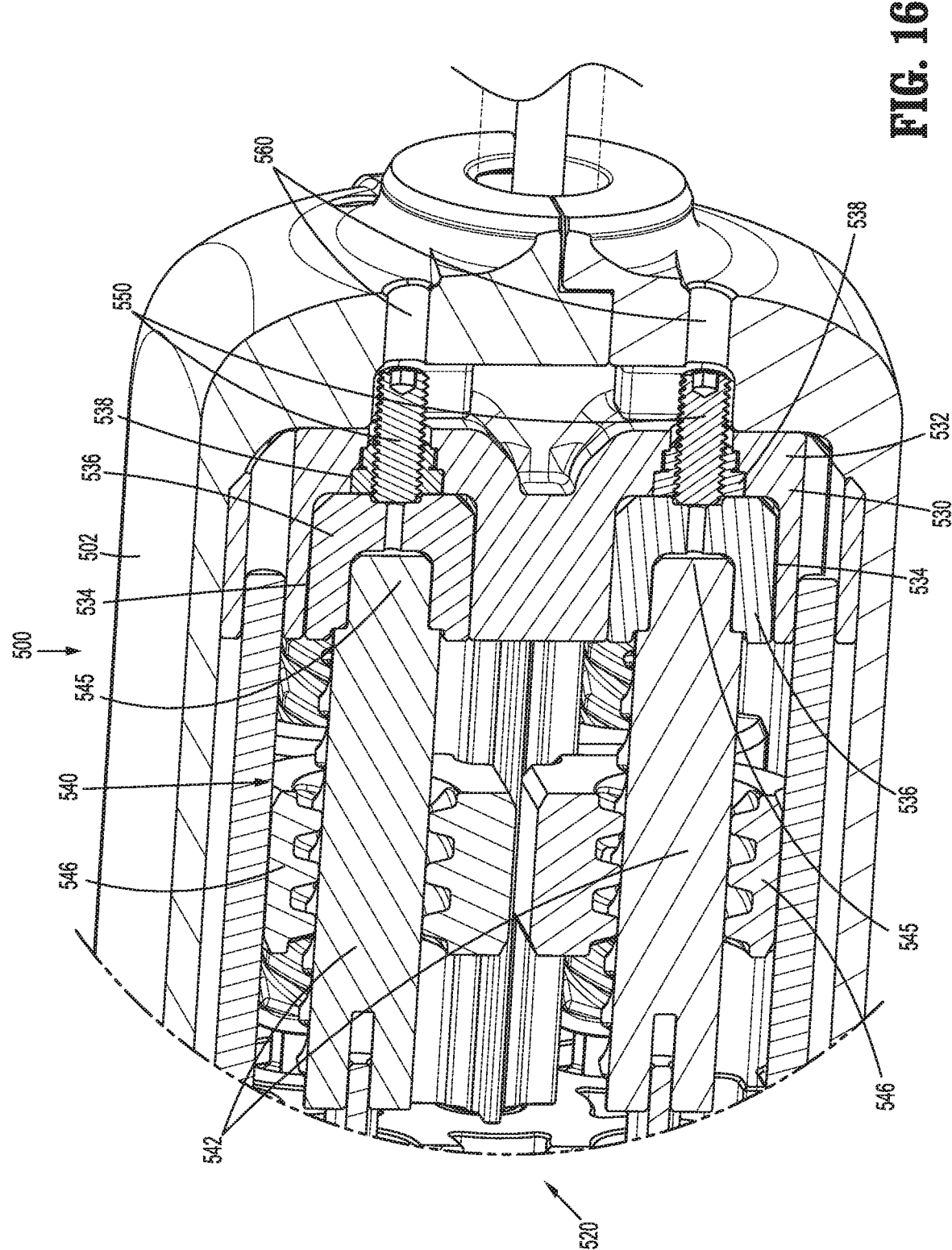
FIG. 16 is an enlarged view of the area of detail indicated as "16" in FIG. 15.

Turning now to FIGS. 10 and 11, pre-tensioning articulation cables 38 (FIG. 3) facilitates accurate articulation of end effector assembly 40 (FIG. 1) and retention of end effector assembly 40 (FIG. 1) in position (whether articulated or aligned). In order to pre-tension articulation cables 38 (FIG. 3), prior to insertion of coupling gears 280, 290 into engagement between the spur gears 248 of each diagonally-opposed pair of spur gears 248, a first opposing diagonal pair of collars 346, e.g., collars 346 of lead screw assemblies 340, 360, are pulled proximally in a similar manner to tension the corresponding articulation cables 38 (FIG. 3) to a pre-tension threshold. Collars 346 may be translated manually, automatically, or semi-automatically using appropriate fixturing (not shown). A suitable force sensing mechanism (not shown) may be utilized to determine the tension on articulation cables 38 (FIG. 3) such that articulation cables 38 (FIG. 3) are pre-tensioned to the pre-tension threshold.

Once the pre-tension threshold has been reached, coupling gear 280 is inserted into meshed engagement with spur gears 248 of proximal gear assemblies 240, 260. With coupling gear 280 inserted in this manner, thereby coupling proximal gear assemblies 240, 260, the articulation cables 38 (FIG. 3) associated with lead screw assemblies 340, 360 are maintained in the pre-tensioned condition due to the fact that lead screw assemblies 340, 360 act in opposite directions and, thus, inhibit de-tensioning of one another.

With reference to FIGS. 2-7, similarly with respect to coupling gear 290 and proximal gear assemblies 250, 270, the second opposing diagonal pair of collars 346, e.g., collars 346 of lead screw assemblies 350, 370, are pulled proximally in a similar manner to tension the corresponding articulation cables 38 (FIG. 3) to the pre-tension threshold. Once the pre-tension threshold has been reached, coupling gear 290 is inserted into meshed engagement with spur gears 248 of proximal gear assemblies 250, 270 to thereby maintain the corresponding articulation cables 38 (FIG. 3) in the pre-tensioned condition.

Referring to FIGS. 12-16, another surgical instrument provided in accordance with the present disclosure is shown generally identified by reference numeral 500. Surgical instrument 500 is similar to surgical instrument 10 (FIG. 1) and, thus, only differences therebetween are described in detail below while similarities are summarily described or omitted entirely.

Surgical instrument 500 generally includes a housing 502, a shaft 503 extending distally from housing 502, an end effector assembly 504 extending distally from shaft 503, and a gearbox assembly 510 disposed within housing 502 and operably associated with end effector assembly 504.

Gearbox assembly 510 of surgical instrument 500 is disposed within housing 502 and includes an articulation sub-assembly 520, a knife drive sub-assembly (not explicitly identified), and a jaw drive sub-assembly (not explicitly identified). Articulation sub-assembly 520 is similar to articulation sub-assembly 200 of surgical instrument 10 (FIGS. 1-11), as detailed above, except as explicitly contradicted below. More specifically, articulation sub-assembly 520 differs in the configuration and manner in which pre-tensioning is achieved.

With respect to articulation sub-assembly 520, the distal dock end 545 of the lead screw 542 of each lead screw assembly 540 extends distally into and is rotationally seated within a corresponding bushing 536 disposed within an aperture 534 of base plate 532 of distal base assembly 530. Distal base assembly 530 defines an internally-threaded nut 538 disposed within each aperture 534 distally-adjacent the busing 536 thereof. A set screw 550 is threadingly engaged within each internally-threaded nut 538. For the purposes herein, "set screw" includes any adjustable setting structure including, for example, a threaded set screw (as illustrated), a lock pin, etc. Set screws 550, thus, may be rotationally driven proximally to abut bushing 536 and urge bushings 536 proximally which, in turn, urge the lead screws 542 proximally. The proximal urging of lead screws 542 moves collars 546 proximally, thereby pulling the associated articulation cables (not shown; see articulation cables 38 (FIG. 3)) proximally to tension the articulation cables. Thus, by rotationally driving set screws 550, the articulation cables may be tensioned to the pre-tensioned threshold.

Access holes 560 defined within housing 502 enable access to set screws 550, e.g., via a suitable driver tool (not shown), to rotationally drive set screws 550 and thus, establish an appropriate pre-tension on the articulation cables (not shown; see articulation cables 38 (FIG. 3)). Thus, with respect to instrument 500, pre-tensioning of the articulation cables is accomplished after assembly is complete, although other configurations are also contemplated.

Figure 17:
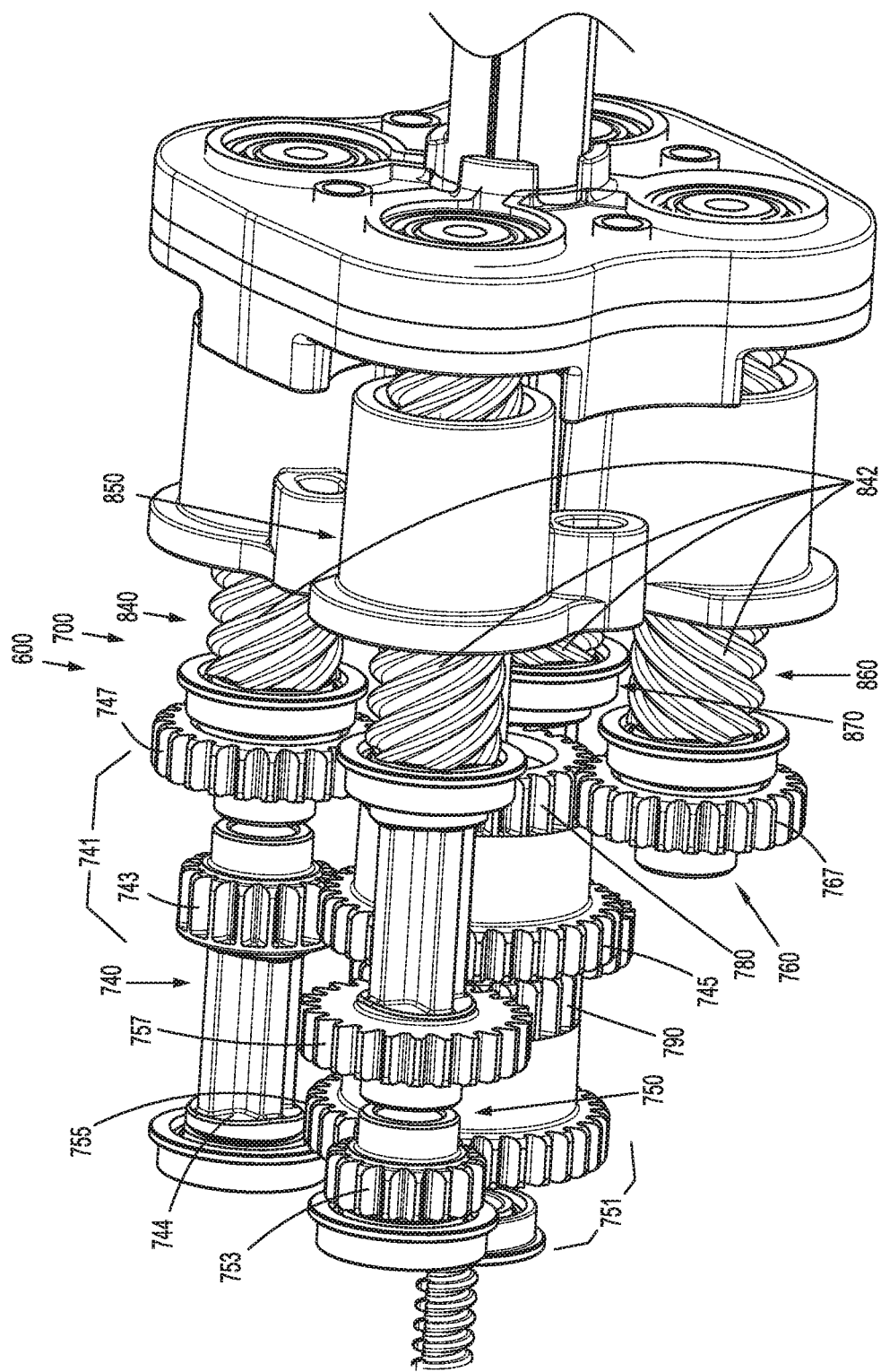
FIG. 17 is a side, perspective view of another articulation assembly, with portions removed, provided in accordance with the present disclosure configured for use with a surgical instrument for mounting on a robotic arm of a robotic surgical system.
Figure 18:
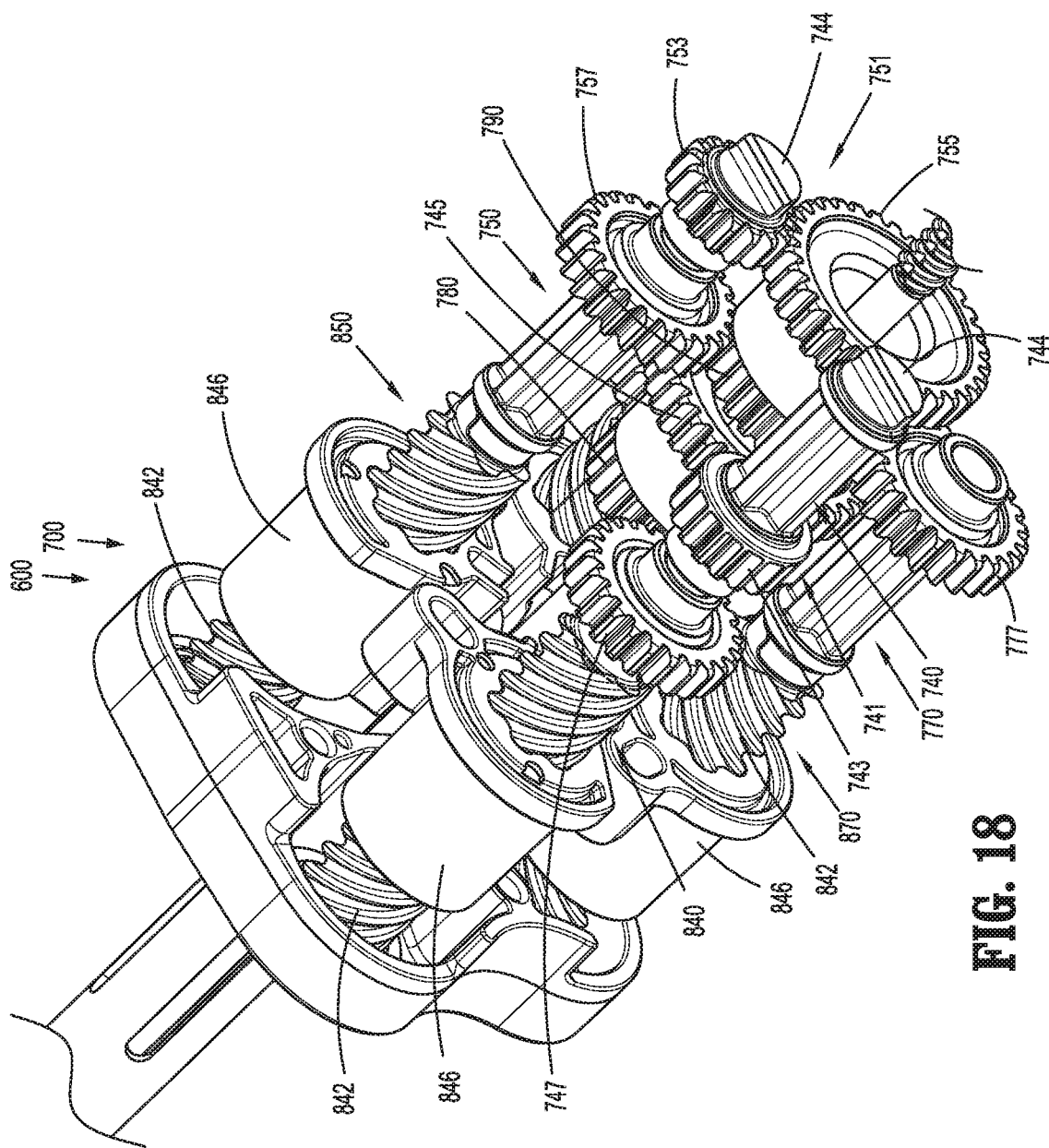
FIG. 18 is a rear, perspective view of the articulation assembly of FIG. 17.

FIGS. 17 and 18 illustrate another gearbox assembly 600 configured, for example, for use with surgical instrument 10 (FIG. 1). Gearbox assembly 600 includes an articulation sub-assembly 700, a knife drive sub-assembly (not shown), and a jaw drive sub-assembly (not shown). Articulation sub-assembly 700 is similar to articulation sub-assembly 200 of surgical instrument 10 (FIGS. 1-11), as detailed above, except as explicitly contradicted below. More specifically, articulation sub-assembly 700 differs in the configuration of proximal gear assemblies 740, 750, 760, 770. That is, rather than including spur gears 248 directly coupled between the input 244 and the corresponding coupling gear 280, 290 as with articulation sub-assembly 200 (FIGS. 2-7), proximal gear assemblies 740, 750 of articulation sub-assembly 700 include gear sets 741, 751 disposed between inputs 744 and coupling gears 780, 790.

Gear set 741 includes a first gear 743 engaged to input 744 of proximal gear assembly 740. First gear 743 is disposed in meshed engagement with a second gear 745 of different size such that a rotational input provided to input 744 rotates first gear 743 to, in turn, rotate second gear 745. A coupling gear 780 is fixed relative to second gear 745 and is disposed in meshed engagement with third gears 747, 767 of proximal gear assemblies 740, 760 (of different size than coupling gear 780) such that rotation of second gear 745 rotates third gears 747, 767. Third gears 747, 767 are engaged with the lead screws 842 of the corresponding lead screw assemblies 840, 860. Thus, proximal gear assemblies 740, 760 operate similarly as detailed above with respect to surgical instrument 10 (FIGS. 1-11) except that amplification or attenuation of the torque and/or motion imparted to lead screw assemblies 840, 860 based upon a rotational input to input 744 is provided. The particular amplification or attenuation of the torque and/or motion is based upon the gear ratios of gears 743, 745, 747, 767.

Gear set 751 is similar to gear set 741 and includes a first gear 753 engaged to input 744 of proximal gear assembly 750. First gear 753 is disposed in meshed engagement with a second gear 755 of different size which, in turn, is fixed relative to a coupling gear 790. Coupling gear 790 is disposed in meshed engagement with third gears 757, 777 of proximal gear assemblies 750, 770 (of different size than coupling gear 790) such that rotation of second gear 755 rotates third gears 757, 777. Third gears 757, 777 are engaged with the lead screws 852 of the corresponding lead screw assemblies 850, 870. Thus, proximal gear assemblies 750, 770 likewise provide amplification or attenuation of the torque and/or motion imparted to lead screw assemblies 850, 870.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An articulation assembly for a surgical instrument, comprising:
   first, second, third, and fourth lead screw assemblies, each lead screw assembly including a lead screw and a collar operably engaged about the lead screw such that rotation of the lead screw translates the collar about the lead screw,
   first, second, third and fourth articulation cables operably coupled to the collars of the first, second, third, and fourth lead screw assemblies, respectively, such that proximal movement of one of the collars about the respective lead screw tensions the corresponding articulation cable and such that distal movement of one of the collars about the respective lead screw de-tensions the corresponding articulation cable;
   first, second, third and fourth proximal gear assemblies coupled to the lead screws of the first, second, third, and fourth lead screw assemblies, respectively;

a first coupling gear coupling the first and third proximal gear assemblies with one another to maintain a pre-tension on the first and third articulation cables; and a second coupling gear coupling the second and fourth proximal gear assemblies with one another to maintain a pre-tension on the second and fourth articulation cables.

2. The articulation assembly according to claim 1, wherein the lead screws of the first and third lead screw assemblies define opposite thread-pitches relative to one another and wherein the lead screws of the second and fourth lead screw assemblies define opposite thread-pitches relative to one another.

3. The articulation assembly according to claim 2, wherein the first coupling gear couples the first and third proximal gear assemblies such that the lead screws of the first and third lead screw assemblies are rotated in similar directions and, thus, such that the collars of the first and third lead screw assemblies are moved in opposite directions, and wherein the second coupling gear couples the second and fourth proximal gear assemblies such that the lead screws of the second and fourth lead screw assemblies are rotated in similar directions and, thus, such that the collars of the second and fourth lead screw assemblies are moved in opposite directions.

4. The articulation assembly according to claim 1, wherein the first coupling gear couples the first and third proximal gear assemblies such that the lead screws of the first and third lead screw assemblies are rotated in similar directions, and wherein the second coupling gear couples the second and fourth proximal gear assemblies such that the lead screws of the second and fourth lead screw assemblies are rotated in similar directions.

5. The articulation assembly according to claim 1, further comprising:

a proximal base assembly, an intermediate base assembly, and a distal base assembly, wherein the first, second, third, and fourth proximal gear assemblies extend between the proximal and intermediate base assemblies, and wherein the first, second, third, and fourth lead screw assemblies extend between the intermediate and distal base assemblies.

6. The articulation assembly according to claim 1, wherein each of the first, second, third, and fourth proximal gear assemblies includes a gear shaft configured to drive rotation of the corresponding lead screw, and a spur gear engaged about the gear shaft, wherein the first coupling gear is disposed in meshed engagement with the spur gear of the first and third proximal gear assemblies and wherein the second coupling gear is disposed in meshed engagement with the spur gear of the second and fourth proximal gear assemblies.

7. The articulation assembly according to claim 1, wherein a first gear set operably couples the first and third proximal gear assemblies with the first coupling gear, the first gear set configured to amplify or attenuate outputs from the first and third proximal gear assemblies to the corresponding lead screws relative to the input to the first proximal gear assembly, and wherein a second gear set operably couples the second and fourth proximal gear assemblies with the second coupling gear, the second gear set configured to amplify or attenuate outputs from the second and fourth proximal gear assemblies to the corresponding lead screws relative to the input to the second proximal gear assembly.

8. A surgical instrument, comprising:

a housing;

a shaft extending distally from the housing, the shaft including an articulating section;

an end effector assembly extending distally from the shaft, the end effector assembly including first and second jaw members, at least the first jaw member movable relative to the second jaw member from a spaced-apart position to an approximated position to grasp tissue therebetween; and an articulation assembly disposed within the housing, the articulation assembly configured to articulate the end effector assembly relative to the housing via first, second, third, and fourth articulation cables extending through the shaft, the articulation assembly including:

first, second, third, and fourth lead screw assemblies, each lead screw assembly including a lead screw and a collar operably engaged about the lead screw such that rotation of the lead screw translates the collar about the lead screw, wherein the first, second, third and fourth articulation cables are operably coupled to the collars of the first, second, third, and fourth lead screw assemblies, respectively, such that proximal movement of one of the collars about the respective lead screw tensions the corresponding articulation cable and such that distal movement of one of the collars about the respective lead screw de-tensions the corresponding articulation cable;

first, second, third and fourth proximal gear assemblies coupled to the lead screws of the first, second, third, and fourth lead screw assemblies, respectively;

a first coupling gear coupling the first and third proximal gear assemblies with one another to maintain a pre-tension on the first and third articulation cables; and a second coupling gear coupling the second and fourth proximal gear assemblies with one another to maintain a pre-tension on the second and fourth articulation cables.

9. The surgical instrument according to claim 8, wherein the lead screws of the first and third lead screw assemblies define opposite thread-pitches relative to one another and wherein the lead screws of the second and fourth lead screw assemblies define opposite thread-pitches relative to one another.

10. The surgical instrument according to claim 9, wherein the first coupling gear couples the first and third proximal gear assemblies such that the lead screws of the first and third lead screw assemblies are rotated in similar directions and, thus, such that the collars of the first and third lead screw assemblies are moved in opposite directions, and wherein the second coupling gear couples the second and fourth proximal gear assemblies such that the lead screws of the second and fourth lead screw assemblies are rotated in similar directions and, thus, such that the collars of the second and fourth lead screw assemblies are moved in opposite directions.

11. The surgical instrument according to claim 8, wherein the first coupling gear couples the first and third proximal gear assemblies such that the lead screws of the first and third lead screw assemblies are rotated in similar directions, and wherein the second coupling gear couples the second and fourth proximal gear assemblies such that the lead screws of the second and fourth lead screw assemblies are rotated in similar directions.

12. The surgical instrument according to claim 8, wherein the articulation assembly further comprises:
a proximal base assembly, an intermediate base assembly, and a distal base assembly, wherein the first, second, third, and fourth proximal gear assemblies extend between the proximal and intermediate base assemblies, and wherein the first, second, third, and fourth lead screw assemblies extend between the intermediate and distal base assemblies.

13. The surgical instrument according to claim 8, wherein each of the first, second, third, and fourth proximal gear assemblies includes a gear shaft configured to drive rotation of the corresponding lead screw, and a spur gear engaged about the gear shaft, wherein the first coupling gear is disposed in meshed engagement with the spur gear of the first and third proximal gear assemblies and wherein the second coupling gear is disposed in meshed engagement with the spur gear of the second and fourth proximal gear assemblies.

14. The surgical instrument according to claim 8, wherein a first gear set operably couples the first and third proximal gear assemblies with the first coupling gear, the first gear set configured to amplify or attenuate outputs from the first and third proximal gear assemblies to the corresponding lead screws relative to the input to the first proximal gear assembly, and wherein a second gear set operably couples the second and fourth proximal gear assemblies with the second coupling gear, the second gear set configured to amplify or attenuate outputs from the second and fourth proximal gear assemblies to the corresponding lead screws relative to the input to the second proximal gear assembly.

15. A robotic surgical system, comprising:
a surgical robot including a robotic arm configured to provide first and second rotational outputs; and
a surgical instrument releasably mountable on the robotic arm, the surgical instrument including:
a housing;
a shaft extending distally from the housing, the shaft including an articulating section;
an end effector assembly extending distally from the shaft, the end effector assembly including first and second jaw members, at least the first jaw member movable relative to the second jaw member from a spaced-apart position to an approximated position to grasp tissue therebetween; and
an articulation assembly disposed within the housing, the articulation assembly configured to articulate the end effector assembly relative to the housing via first, second, third, and fourth articulation cables extending through the shaft, the articulation assembly including:
first, second, third, and fourth lead screw assemblies, each lead screw assembly including a lead screw and a collar operably engaged about the lead screw such that rotation of the lead screw translates the collar about the lead screw, wherein the first, second, third and fourth articulation cables are operably coupled to the collars of the first, second, third, and fourth lead screw assemblies, respectively, such that proximal movement of one of the collars about the respective lead screw tensions the corresponding articulation cable and such that distal movement of one of the collars about the respective lead screw de-tensions the corresponding articulation cable;
first, second, third and fourth proximal gear assemblies coupled to the lead screws of the first, second, third, and fourth lead screw assemblies, respectively, the first and second input gears configured to receive the first and second rotational outputs, respectively;
a first coupling gear coupling the first and third proximal gear assemblies with one another to maintain a pre-tension on the first and third articulation cables; and
a second coupling gear coupling the second and fourth proximal gear assemblies with one another to maintain a pre-tension on the second and fourth articulation cables.

16. The robotic surgical system according to claim 15, wherein the lead screws of the first and third lead screw assemblies define opposite thread-pitches relative to one another and wherein the lead screws of the second and fourth lead screw assemblies define opposite thread-pitches relative to one another.

17. The robotic surgical system according to claim 16, wherein the first coupling gear couples the first and third proximal gear assemblies such that the lead screws of the first and third lead screw assemblies are rotated in similar directions and, thus, such that the collars of the first and third lead screw assemblies are moved in opposite directions, and wherein the second coupling gear couples the second and fourth proximal gear assemblies such that the lead screws of the second and fourth lead screw assemblies are rotated in similar directions and, thus, such that the collars of the second and fourth lead screw assemblies are moved in opposite directions.

18. The robotic surgical system according to claim 15, wherein the articulation assembly further comprises:
a proximal base assembly, an intermediate base assembly, and a distal base assembly, wherein the first, second, third, and fourth proximal gear assemblies extend between the proximal and intermediate base assemblies, and wherein the first, second, third, and fourth lead screw assemblies extend between the intermediate and distal base assemblies.

19. The robotic surgical system according to claim 15, wherein each of the first, second, third, and fourth proximal gear assemblies includes a gear shaft configured to drive rotation of the corresponding lead screw, and a spur gear engaged about the gear shaft, wherein the first coupling gear is disposed in meshed engagement with the spur gear of the first and third proximal gear assemblies and wherein the second coupling gear is disposed in meshed engagement with the spur gear of the second and fourth proximal gear assemblies.

20. The robotic surgical system according to claim 15, wherein a first gear set operably couples the first and third proximal gear assemblies with the first coupling gear, the first gear set configured to amplify or attenuate outputs from the first and third proximal gear assemblies to the corresponding lead screws relative to the input to the first proximal gear assembly, and wherein a second gear set operably couples the second and fourth proximal gear assemblies with the second coupling gear, the second gear set configured to amplify or attenuate outputs from the second and fourth proximal gear assemblies to the corresponding lead screws relative to the input to the second proximal gear assembly.

* * * * *